(12) United States Patent
Howarth et al.

(10) Patent No.: US 10,889,622 B2
(45) Date of Patent: Jan. 12, 2021

(54) PEPTIDE LIGASE AND USE THEREOF

(71) Applicant: Oxford University Innovation Limited, Oxford (GB)

(72) Inventors: Mark Howarth, Oxford (GB); Can M. Buldun, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 16/603,850

(22) PCT Filed: Apr. 10, 2018

(86) PCT No.: PCT/GB2018/050943
§ 371 (c)(1),
(2) Date: Oct. 9, 2019

(87) PCT Pub. No.: WO2018/189517
PCT Pub. Date: Oct. 18, 2018

(65) Prior Publication Data
US 2020/0115422 A1 Apr. 16, 2020

(30) Foreign Application Priority Data
Apr. 10, 2017 (GB) .................................. 1705750.6

(51) Int. Cl.
*C07K 1/00* (2006.01)
*C07K 14/315* (2006.01)
*C12N 9/00* (2006.01)

(52) U.S. Cl.
CPC ............ *C07K 14/3156* (2013.01); *C12N 9/93* (2013.01)

(58) Field of Classification Search
CPC .................................................. C07K 14/3156
See application file for complete search history.

(56) References Cited

U.S. PATENT DOCUMENTS

2014/0017727 A1  1/2014 Manetti et al.

FOREIGN PATENT DOCUMENTS

| WO | 2009/016515 A2 | 2/2009 |
| WO | 2011/098772 A1 | 8/2011 |
| WO | 2016/112921 A1 | 7/2016 |
| WO | 2016/193746 A1 | 12/2016 |

OTHER PUBLICATIONS

International Research Report & Written Opinion for PCT/GB2018/050943, dated Jul. 26, 2018, pp. 1-20.
Jacob O. Fierer et al., "SpyLigase peptide-peptide ligation polymerizes affibodies to enhance magnetic cancer cell rapture", PNAS, pp. E1176-E1181, published online Mar. 17, 2014.
Brune et al., 2016, Scientific Reports 6, 19234, "Plug-and-Display: decoration of Virus-Like Particles via isopeptide bonds for modular immunization", pp. 1-13.
Antos et al., J. Am. Chem. Soc. 2009, vol. 131(31), pp. 10800-10801, "Site-Specific N- and C-Terminal Labeling of a Single Polypeptide Using Sortases of Different Specificity".
Chen et al., Proc. Natl Acad. Sci. USA, 2011, vol. 108(28), pp. 11399-11404, "A general strategy for the evolution of bond-forming enzymes using yeast display".
Siegmund V et al., Sci Rep. Dec. 16, 2016;6:39291, "Spontaneous Isopeptide Bond Formation as a Powerful Tool for Engineering Site-Specific Antibody-Drug Conjugates".
Buldun et al., J. Am. Chem. Soc. Feb. 28, 2018;140(8):3008-3018, "SnoopLigase catalyzes peptide-peptide locking and enables solid-phase conjugate isolation".
Botyanszki et al., 2015, Biotechnology and Bioengineering, 2016-2024, vol. 112, No. 10, Oct. 2015, "Engineered Catalytic Biofilms: Site-Specific Enzyme Immobilization onto *E. coli*Curli Nanofibers".
Stranges et al., 2016, Proc Natl Acad Sci U S A 113, E6749-E6756, "Design and characterization of a nanopore-coupled polymerase for single-molecule DNA sequencing by synthesis on an electrode array".
Schoene et al., 2016, Scientific Reports 6, 21151, "SpyRing interrogation: analyzing how enzyme resilience can be achieved with phytase and distinct cyclization chemistries", pp. 1-2.
Thrane et al., 2016, Journal of Nanobiotechnology 14, 30, "Bacterial superglue enables easy development of efficient virus-like particle based vaccines", pp. 1-16.
Veggiani et al., 2016 Proc Natl Acad Sci U S A 113, 1202-1207, "Programmable polyproteams built using twin peptide superglues".
Alves NJ et al., J Vis Exp. Nov. 16, 2016;(117), "Directed Protein Packaging within Outer Membrane Vesicles from *Escherichia coli*: Design, Production and Purification", pp. 1-10.
Liu X et al., Sci Rep. Nov. 29, 2016;6:38019., "Engineering Genetically-Encoded Mineralization and Magnetism via Directed Evolution", pp. 1-10.
Hyojin Moon et al., Chem Commun (Camb). Nov. 29, 2016;52(97):14051-14054., "Plug-and-Playable Fluorescent Cell Imaging Modular Toolkits Using the Bacterial Superglue, SpyTag/SpyCatcher".
Janitzek CM et al., Malar J. Nov. 8, 2016;15(1):545., "Bacterial superglue generates a full-length circumsporozoite protein virus-like particle vaccine capable of inducing high and durable antibody responses".

(Continued)

Primary Examiner — Albert M Navarro
(74) Attorney, Agent, or Firm — Thomas|Horstemeyer, LLP

(57) ABSTRACT

The present invention relates to a polypeptide that is capable of promoting the covalent conjugation of two peptide tags or linkers and in particular to a polypeptide comprising: a) an amino acid sequence as set forth in SEQ ID NO: 1; or b) an amino acid sequence with at least 80% sequence identity to a sequence as set forth in SEQ ID NO: 1, wherein said amino acid sequence comprises a glutamic acid at position 61 and one or more of the following: 1) proline at position 66; 2) proline at position 95; 3) glycine at position 96; and 4) valine at position 97, wherein the specified amino acid residues are at positions equivalent to the positions in SEQ ID NO: 1 and wherein said polypeptide is capable of promoting the formation of an isopeptide bond between the lysine residue at position 9 of SEQ ID NO: 2 and the asparagine residue at position 17 of SEQ ID NO: 3.

18 Claims, 17 Drawing Sheets
Specification includes a Sequence Listing.

(56) References Cited

OTHER PUBLICATIONS

Xiong et al, Chinese Journal of Biochemistry and Molecular Biology (2016), 32 (10): 1141-1149 (partial translation).
Schmid-Burgk et al., Nat Commun. Jul. 28, 2016;7:12338., "CRISPaint allows modular base-specific gene tagging using a ligase-4-dependent mechanism".
Dorval Courchesne et al., ACS Biomater. Sci. Eng. 2017, 3, 5, 733-741, "Scalable Production of Genetically Engineered Nanofibrous Macroscopic Materials via Filtration".
Pardee K et al., Cell. Sep. 22, 2016;167(1):248-259, "Portable, On-Demand Biomolecular Manufacturing".
Schloss et al., ACS Biomater. Sci. Eng. 2016, 2, 11, 1856-1861, "Fabrication of Modularly Functionalizable Microcapsules Using Protein-Based Technologies".
Si M et al., PLoS One. Sep. 22, 2016;11(9):e0162318., "SpyTag/SpyCatcher Cyclization Enhances the Thermostability of Firefly Luciferase".
Lakshmanan A et al., ACS Nano. Aug. 23, 2016;10(8):7314-22., "Molecular Engineering of Acoustic Protein Nanostructures".
Giessen TW, Silver R, Chembiochem. Oct. 17, 2016;17(20):1931-1935., "A Catalytic Nanoreactor Based on in Vivo Encapsulation of Multiple Enzymes in an Engineered Protein Nanocompartment".
Gao X et al., Biomacromolecules. Sep. 12, 2016;17(9):2812-9., "Engineering Protein Hydrogels Using SpyCatcher-SpyTag Chemistry".
Min D et al., Protein Sci. Aug. 2016;25(8):1535-44., "Methods and Applications—A simple DNA handle attachment method for single molecule mechanical manipulation experiments".
Fuller CW et al., Proc Natl Acad Sci U S A. May 10, 2016;113(19):5233-8., "Real-time single-molecule electronic DNA sequencing by synthesis using polymer-tagged nucleotides on a nanopore array".
Alves NJ et al., Sci Rep. Apr. 27, 2016;6:24866, "Protecting enzymatic function through directed packaging into bacterial outer membrane vesicles", pp. 1-10.
Wang J et al., Biotechnol Biofuels. Mar. 31, 2016;9:79., "Enhanced thermal stability of lichenase from Bacillus subtilis 168 by SpyTag/SpyCatcher-mediated spontaneous cyclization".
Liu Z et al., Oncoimmunology. Mar. 10, 2016;5(6):e1147641, "A novel dendritic cell targeting HPV16 E7 synthetic vaccine in combination with PD-L1 blockade elicits therapeutic antitumor immunity in mice".
Wang XW, Zhang WB., Angew Chem Int Ed Engl. Mar. 1, 2016;55(10):3442-6., "Cellular Synthesis of Protein Catenanes".
Dovala D et al., Protein Expr Purif. Jan. 2016;117:44-51., "Rapid analysis of protein expression and solubility with the SpyTag-SpyCatcher system".
Alves NJ et al., ACS Appl Mater Interfaces. Nov. 11, 2015;7(44):24963-72, "Bacterial Nanobioreactors-Directing Enzyme Packaging into Bacterial Outer Membrane Vesicles".
Bedbrook CN et al., Chem Biol. Aug. 20, 2015;22(8):1108-21, "Genetically Encoded Spy Peptide Fusion System to Detect Plasma Membrane-Localized Proteins in vivo".
Malden M et al., Elife. Jun. 2, 2015;4., "An internal thioester in a pathogen surface protein mediates covalent host binding".
Leonard JD, Narlikar GJ., Mol Cell. Mar. 5, 2015;57(5):850-9., "A Nucleotide-Driven Switch Regulates Flanking DNA Length Sensing by a Dimeric Chromatin Remodeler".
Liu Z et al., Sci Rep. Dec. 1, 2014;4:7266., "A novel method for synthetic vaccine construction based on protein assembly".
Nguyen PQ et al., Nat Commun. Sep. 17, 2014;5:4945., "Programmable biofilm-based materials from engineered curli nanofibres".
Sun F et al., Proc Natl Acad Sci U S A. Aug. 5, 2014;111(31):11269-74., "Synthesis of bioactive protein hydrogels by genetically encoded SpyTag-SpyCatcher chemistry".
Chen AY et al., Nat Mater. May 2014;13(5):515-23., "Synthesis and patterning of tunable multiscale materials with engineered cells".
Zhang WB et al., J Am Chem Soc. Sep. 18, 2013;135(37):13988-97., "Controlling Macromolecular Topology with Genetically Encoded SpyTag-SpyCatcher Chemistry".
Gilbert et al., ACS Synth. Biol. 2017, 6, 6, 957-967, "Extracellular Self-Assembly of Functional and Tunable Protein Conjugates from Bacillus subtilis".
Fairhead M et al., Journal of the American Chemical Society Sep. 3, 2014;136(35):12355-63., "SpyAvidin Hubs Enable Precise and Ultrastable Orthogonal Nanoassembly".
Schoene C et al., Angewandte Chemie. Jun. 10, 2014;53(24):6101-4., "SpyTag/SpyCatcher Cyclization Confers Resilience to Boiling on a Mesophilic Enzyme".
Li L et al., Journal of Molecular Biology. Jan. 23, 2014;426(2)309-17., "Structural Analysis and Optimization of the Covalent Association between SpyCatcher and a Peptide Tag".
Reddington and Howarth, Current Opinion in Chemical Biology (2015); 29, 94-99., "Secrets of a covalent interaction for biomaterials and biotechnology: SpyTag and SpyCatcher".
Keeble et al., Angew Chem Int Ed (2017), 56, 52, 16521-16525., "Evolving Accelerated Amidation by SpyTag/SpyCatcher to Analyze Membrane Dynamics".
Zakeri et al., J Am Chem Soc (2010), 132, 32, 4526-4527., "Spontaneous Intermolecular Amide Bond Formation between Side Chains for Irreversible Peptide Targeting".
Zakeri et al., 2012, Proc Natl Acad Sci U S A 109, E690-697., "Peptide tag forming a rapid covalent bond to a protein, through engineering a bacterial adhesin".
Andersson AC et al., Sci Rep. Mar. 15, 2019;9(1):4625, "SnoopLigase peptide-peptide conjugation enables modular vaccine assembly", pp. 1-13.
Brune et al., Bioconjug Chem. May 17, 2017;28(5):1544-1551, "Dual Plug-and-Display Synthetic Assembly Using Orthogonal Reactive Proteins for Twin Antigen Immunization".

A

B

A

B

A

B

PEPTIDE LIGASE AND USE THEREOF

CROSS-REFERENCE TO RELATED APPLICATIONS

This application is the National Stage of International Application No. PCT/GB2018/050943, filed Apr. 10, 2018, which claims the priority to GB 1705750.6, filed Apr. 10, 2017, which are entirely incorporated herein by reference.

The present invention relates to a polypeptide that is capable of promoting the covalent conjugation of two peptide tags or linkers. In particular, the polypeptide of the invention is capable of promoting the formation of an isopeptide bond between two specific peptide tags or linkers, i.e. the polypeptide of the invention may be viewed as a peptide ligase. The invention also provides peptide tags or linkers that may be conjugated (i.e. covalently joined, coupled or linked via an isopeptide bond) efficiently by the peptide ligase of the invention. Nucleic acid molecules encoding said polypeptide (peptide ligase) and peptide tags, vectors comprising said nucleic acid molecules and host cells comprising said vectors and nucleic acid molecules are also provided. A kit comprising said peptide tags, polypeptides and/or nucleic acid molecules/vectors is also provided. A method of producing said polypeptide (peptide ligase) and/or peptide tags and the uses of the polypeptide and peptide tags of the invention are also provided.

Biological events usually depend on the cooperative activity of multiple proteins and the precise arrangement of proteins in complexes influences and determines their function. Thus, the ability to arrange individual proteins in a complex in a controlled manner represents a useful tool in characterising protein functions. Moreover, the conjugation of multiple proteins to form a so-called "fusion protein" can result in molecules with useful characteristics. For instance, clustering a single kind of protein often greatly enhances biological signals, e.g. the repeating antigen structures on vaccines. Clustering proteins with different activities can also result in complexes with improved activities, e.g. substrate channelling by enzymes.

Peptide tags are convenient tools for protein analysis and modification because their small size minimizes the perturbation to protein function. Peptide tags are simple to genetically encode and their small size reduces interference with other interactions, cost of biosynthesis and introduction of immunogenicity. However, interactions between peptide tags are rarely of high affinity, which limits their utility in the formation of stable complexes.

Proteins that are capable of spontaneous isopeptide bond formation have been advantageously used to develop peptide tag/binding partner pairs which covalently bind to each other and provide irreversible interactions (see e.g. WO2011/098772 and WO 2016/193746 both herein incorporated by reference). In this respect, proteins which are capable of spontaneous isopeptide bond formation may be expressed as separate fragments, to give a peptide tag and a binding partner for the peptide tag, where the two fragments are capable of covalently reconstituting by isopeptide bond formation. The isopeptide bond formed by the peptide tag and binding partner pairs is stable under conditions where non-covalent interactions would rapidly dissociate, e.g. over long periods of time (e.g. weeks), at high temperature (to at least 95° C.), at high force, or with harsh chemical treatment (e.g. pH 2-11, organic solvent, detergents or denaturants).

Isopeptide bonds are amide bonds formed between carboxyl/carboxamide and amino groups, where at least one of the carboxyl or amino groups is outside of the protein main-chain (the backbone of the protein). Such bonds are chemically irreversible under typical biological conditions and they are resistant to most proteases. As isopeptide bonds are covalent in nature, they result in the strongest measured protein interactions.

In brief, a peptide tag/binding partner pair may be derived from a protein capable of spontaneously forming an isopeptide bond (an isopeptide protein), wherein the domains of the protein are expressed separately to produce a peptide tag that comprises one of the residues involved in the isopeptide bond (e.g. a lysine) and a peptide binding partner (or "Catcher") that comprises the other residue involved in the isopeptide bond (e.g. an asparagine or aspartate) and at least one other residue required to form the isopeptide bond (e.g. a glutamate). Mixing the peptide tag and binding partner results in the spontaneous formation of an isopeptide bond between the tag and binding partner. Thus, by separately fusing the peptide tag and binding partner to different molecules, e.g. proteins, it is possible to covalently link said molecules together via an isopeptide bond formed between the peptide tag and binding partner.

Whilst the peptide tag/binding partner pairs derived from isopeptide proteins (also known as Tag/Catcher systems, e.g. SpyTag and SpyCatcher) have found diverse uses around the world, their utility has been limited by the size of binding partners ("Catchers") as fusion partners. Peptide tag binding partners ("Catchers") derived from isopeptide proteins typically comprise more than 80 amino acids, such as at least 90 or 100 amino acids, which results in a number of problems.

For instance, Tag/Catcher systems have been shown to find utility in decorating virus-like particles with antigens (see e.g. Brune et al. 2016, Scientific Reports, 6:19234), wherein a virus-like particle is fused to a Catcher to produce a vaccine system platform that can be used to display any antigen fused to the Tag. However, the large size of "Catchers" means that they are more likely to have high immunogenicity, which may impair the use of Tag/Catcher systems in the production of vaccine system platforms. Vaccines produced using such platforms may result in the induction of antibodies or T cells to the Catcher rather than the target antigen. Such immunogenicity also may prohibit the use of the same vaccine system platform for sequential vaccination against two separate diseases.

The large size of Catchers in Tag/Catcher systems also imparts a limitation on their location in a fusion molecule, e.g. a fusion protein. Catchers generally need to be fused at protein termini to avoid interference with protein folding. Moreover, Catchers look like partially folded proteins and so may reduce expression yields.

A further important limitation of Tag/Catcher systems caused by the size of the Catcher relates to the inducibility of the reaction between the Tag and Catcher. Typically, Tag and Catcher protein fusions react spontaneously when expressed in cells and in some circumstances, it would be advantageous to avoid or control such reactions.

Accordingly, there is a desire to develop peptide tag systems with the advantageous properties associated with Tag/Catcher systems derived from isopeptide proteins, i.e. peptide tags that form a stable and robust covalent bond as discussed above, whilst avoiding the problems associated with the large size of peptide binding partners (Catchers).

It has been found that it is possible to express the domains of an isopeptide protein comprising the residues involved in isopeptide bond formation separately, i.e. as three separate fragments, i.e. two peptides and a polypeptide (see e.g. Fierer et al. 2014, PNAS E1176-E1181). In brief, one peptide tag (KTag) comprises one of the residues involved in the isopeptide bond (e.g. a lysine), a second peptide tag (SpyTag) comprises the other residue involved in the isopeptide bond (e.g. an aspartate) and a polypeptide (SpyLigase) comprises the residue involved in mediating the isopeptide bond formation (e.g. a glutamate). Mixing all three fragments, i.e. both peptides and the polypeptide, results in the formation of an isopeptide bond between the two peptides comprising the residues that react to form the isopeptide bond, i.e. SpyTag and KTag. Thus, the polypeptide (SpyLigase) mediates the conjugation of the peptide tags but does not form part of the resultant structure, i.e. the polypeptide is not covalently linked to the peptide tags. As such, the polypeptide may be viewed as a protein ligase or peptide ligase.

The SpyLigase system described above is, in theory, particularly useful as it minimises the size of the peptide tags that need to be fused to the molecule, e.g. protein of interest, thereby reducing the possibility of unwanted interactions caused by the addition of the peptide tag binding partner (Catcher) discussed above, e.g. misfolding. However, the SpyLigase system shows a poor yield of conjugation between peptide partners (typically 50% or less) and has low activity above 4° C. Moreover, the utility of SpyLigase is limited by its inability to function in a broad range of conditions, e.g. buffers, and the slow reaction rate, typically about 24 hours (Fierer et al. 2014, supra).

The present inventors have developed a peptide ligase system, i.e. a peptide ligase and a pair of peptide tags, from the C-terminal domain of the *Streptococcus pneumoniae* adhesin, RrgA (SEQ ID NO: 4), which naturally contains a spontaneous isopeptide bond between lysine and asparagine, promoted by an apposed glutamic acid. As discussed below, and in detail in the Examples, a number of steps were required to generate the peptide ligase system of the invention.

Firstly, the inventors had to select an appropriate isopeptide protein from a wide range of candidates for modification and subsequently determine the appropriate locations at which to split the protein. In this respect, the C-terminal domain of RrgA contains 8 β-strands and isolation of the domain comprising the glutamic acid residue responsible for promoting the formation of the isopeptide bond from the domains containing the reactive residues resulted in the removal of 3 β-strands (see FIG. 1A). The removal of 3 β-strands from a small protein domain is a major modification and the truncated polypeptide (i.e. the putative peptide ligase also known as RrgALigase) was thought to have poor stability. Notably, the truncated polypeptide showed low solubility (particularly in solutions comprising NaCl, e.g. phosphate-buffered saline) and showed low ligase activity. Indeed, the truncated polypeptide (RrgALigase) was fused to maltose binding protein (MBP) to improve RrgALigase's solubility and facilitate characterisation and modification of the protein.

Thus, a second aspect in the development of the peptide ligase system of the invention required the design and introduction of various modifications (i.e. mutations) to the separate components derived from the isopeptide protein, particularly the putative peptide ligase. Not only did the modifications result in an active peptide ligase capable of promoting the formation of an isopeptide bond between two peptide tags, but it was surprisingly determined that they also improved the solubility and activity of the peptide ligase domain, i.e. when the modified peptide ligase was not linked to MBP the modified peptide ligase was soluble and active in a wide range of conditions. Moreover, the peptide ligase system of the present invention shows improved properties relative to the SpyLigase system discussed above, e.g. higher yield (i.e. 95%), broad range of reaction conditions (temperature, e.g. up to 37° C., a range of buffers etc.), faster reaction rate (i.e. high yield in about 4 hours), and the ability to function in the absence of a chemical chaperone, such as TMAO (trimethylamine N-oxide).

Notably, the peptide ligase system of the invention represents an improvement over peptide ligase systems, e.g. sortase and transglutaminase, evolved by nature over long time-periods. For example, sortase enzymes are present in diverse Gram-positive bacteria that diverged more than 2 billion years ago (Antos et al., J. Am. Chem. Soc. 2009, vol. 131(31), pp. 10800-10801). In fact, the inventors have unexpectedly found that the peptide ligase system of the invention has a high yield even at relatively low concentrations of peptide tag. By way of comparison, the peptide ligase system of the present invention is efficient at peptide tag concentrations that are ten-fold lower than the concentration of the oligoglycine-reactive partner that is typically used with sortase (Chen et al., Proc. Natl Acad. Sci. USA, 2011, vol. 108(28), pp. 11399-11404).

Thus, in one aspect, the present invention therefore provides a polypeptide comprising:

a) an amino acid sequence as set forth in SEQ ID NO: 1; or b) an amino acid sequence with at least 80% sequence identity to a sequence as set forth in SEQ ID NO: 1, wherein said amino acid sequence comprises a glutamic acid at position 61 and one or more of the following:

1) proline at position 66;
2) proline at position 95;
3) glycine at position 96; and
4) valine at position 97, wherein the specified amino acid residues are at positions equivalent to the positions in SEQ ID NO: 1 and wherein said polypeptide is capable of promoting the formation of an isopeptide bond between the lysine residue at position 9 of SEQ ID NO: 2 and the asparagine residue at position 17 of SEQ ID NO: 3.

As the polypeptide of the invention mediates the covalent conjugation of the peptide tags of the invention (SEQ ID NOs: 2 and 3, as discussed below), it may be viewed as a peptide ligase. Additionally or alternatively, the polypeptide of the invention could be viewed as a catalyst that promotes the formation of an isopeptide bond between the peptide tags of the invention. In this respect, a catalyst may be defined as a molecule that enables a reaction to occur without changing its own composition and it is believed that the structure of the polypeptide of the invention following its interaction with the peptide tags of the invention, and subsequent promotion of the formation of the isopeptide bond between said peptide tags, is exactly the same as its structure prior to the interaction. Thus, the polypeptide of the invention may be viewed as a peptide ligase that catalyses the formation of an isopeptide bond between the peptide tags of the invention.

As shown in the Examples, a large number of modifications were skilfully designed and introduced into the truncated RrgA C-terminal domain polypeptide (putative ligase or RrgALigase) and tested to determine their effects on the ligase activity of the polypeptide. The inventors determined that only selected modifications resulted in an improvement in the activity of the ligase activity (see FIG. 2A). Moreover, it was found that each selected modification independently improves the activity of the ligase.

Accordingly, in some embodiments, the polypeptide of the invention may comprise an amino acid sequence with at least 80% sequence identity to a sequence as set forth in SEQ ID NO: 1, wherein said amino acid sequence comprises a glutamic acid at position 61 and two, three or four of the following:
1) proline at position 66;
2) proline at position 95;
3) glycine at position 96; and
4) valine at position 97.

Thus, for instance, the polypeptide variants of the invention may comprise at least proline residues at positions 66 and 95. In some embodiments, the polypeptide variants of the invention may comprise at least a proline residue at position 66 and/or 95 and a glycine residue at position 96. In still further embodiments, the polypeptide variants of the invention may comprise at least a proline residue at position 66 and/or 95 and a valine residue at position 97. In a particularly preferred embodiment, the polypeptide of the invention comprises an amino acid sequence with at least 80% sequence identity to a sequence as set forth in SEQ ID NO: 1 and all of the following:
1) glutamic acid at position 61;
2) proline at position 66;
3) proline at position 95;
4) glycine at position 96; and
5) valine at position 97.

In still further embodiments, the polypeptide variants of the invention may comprise a threonine residue at position 100.

Thus, the polypeptide (peptide ligase) of the present invention particularly may be at least 80% identical to the exemplified sequence as set forth in SEQ ID NO: 1 and more particularly is at least 85, 90, 95, 96, 97, 98 or 99% identical to SEQ ID NO: 1, wherein the polypeptide variant comprises a glutamic acid residue at position 61 (or an equivalent position) and one or more of:
1) proline at position 66;
2) proline at position 95;
3) glycine at position 96; and
4) valine at position 97,
or their equivalent positions, as defined below.

The polypeptide of the invention is capable of promoting the formation of an isopeptide bond between the lysine residue at position 9 of SEQ ID NO: 2 and the asparagine residue at position 17 of SEQ ID NO: 3 under conditions that are suitable for the formation of an isopeptide bond between said peptide tags and/or suitable for the ligase activity of the polypeptide of the invention. It is evident from the Examples below that the polypeptide of the invention is active under a range of conditions. For instance, in Tris borate (TB) buffer at a pH of 6.0-9.0, e.g. 7.0-9.0, 7.25-8.75, such as about 7.5-8.5, over a wide range of temperatures, e.g. 0-40° C., such as 5-39, 10-38, 15-37° C., e.g. 1, 2, 3, 4, 5, 10, 12, 15, 18, 20, 22, 25, 27, 29, 31, 33, 35 or 37° C., preferably about 15° C. The polypeptide is functional in the presence of extracellular concentrations of NaCl, e.g. about 150 mM NaCl or less. However, in some embodiments, it may be preferable to perform ligation reactions in the absence of NaCl. The polypeptide of the invention is also active in the presence of the commonly used detergents, such as Tween 20 and Triton X-100 up to a concentration of about 2% (v/v). Moreover, the polypeptide is active in the presence of glycerol at concentrations of up to about at least 40% (v/v). Thus, in some embodiments, it may be preferable to perform ligation reactions in the presence of glycerol, e.g. about 5-50%, 10-40%, preferably about 15-30% (v/v). The skilled person would readily be able to determine other suitable conditions.

Thus, in some embodiments, conditions that are suitable for the formation of an isopeptide bond between said peptide tags and/or suitable for the ligase activity of the polypeptide of the invention includes any conditions in which contacting the polypeptide of the invention with the peptide tags as defined herein results in the formation of an isopeptide bond between said peptide tags, particularly between the lysine residue at position 9 of SEQ ID NO: 2 and the asparagine residue at position 17 of SEQ ID NO: 3. For instance, contacting said polypeptide and peptide tags in buffered conditions, e.g. in a buffered solution or on a solid phase (e.g. column) that has been equilibrated with a buffer, such as Tris borate buffer. The step of contacting may be at any suitable pH, such as pH 6.0-9.0, e.g. 6.5-9.0, such as pH 6.8, 7.0, 7.2, 7.4, 7.6, 7.8, 8.0, 8.2, 8.4, 8.6 or 8.8. Additionally or alternatively, the step of contacting may be at any suitable temperature, such as about 0-40° C., e.g. about 1-39, 2-38, 3-37, 4-36, 5-35, 6-34, 7-33, 8-32, 9-31 or 10-30° C., e.g. about 10, 12, 15, 18, 20, 22 or 25° C., preferably about 15° C. In some embodiments, the step of contacting may be in the absence of NaCl. In some embodiments, the step of contacting may be in the presence of glycerol, e.g. about 5-50%, 10-40%, preferably about 15-30% (v/v).

In some embodiments, contacting the polypeptide and peptide tags as defined herein "under conditions that are suitable for the formation of an isopeptide bond" includes contacting said polypeptide and peptide tags in the presence of a chemical chaperone, e.g. a molecule that enhances or improves the reactivity of the polypeptide and/or peptide tags. In some embodiments, the chemical chaperone is TMAO (trimethylamine N-oxide). In some embodiments, the chemical chaperone, e.g. TMAO, is present in the reaction at a concentration of at least about 0.2 M, e.g. at least 0.3, 0.4, 0.5, 1.0, 1.5, 2.0 or 2.5 M, e.g. about 0.2-3.0 M, 0.5-2.0 M, 1.0-1.5 M.

The polypeptide of the invention thus encompasses mutant forms of the polypeptide (i.e. referred to herein as homologues, variants or derivatives) which are structurally similar to the exemplified polypeptide set forth in SEQ ID NO: 1 and are able to function as a peptide ligase, particularly capable of promoting the formation of an isopeptide bond between the peptide tags of the invention (peptides comprising amino acid sequences as set forth in SEQ ID NOs: 2 and 3) under suitable conditions as defined above. In cases where a polypeptide variant comprises mutations, e.g. deletions or insertions, relative to SEQ ID NO: 1, the residues specified above are present at equivalent amino acid positions in the variant polypeptide sequence. In a preferred embodiment, deletions in the polypeptide variants of the invention are not N-terminal and/or C-terminal truncations.

Thus, in some embodiments, a polypeptide variant of the present invention may differ from SEQ ID NO: 1 by for example 1 to 20, 1 to 15, 1 to 10, 1 to 8, 1 to 6, 1 to 5, 1 to 4, e.g. 1, 2 to 3 amino acid substitutions, insertions and/or deletions, preferably substitutions. In some embodiments, any other mutations that are present in the polypeptide (peptide ligase) of the present invention may be conservative amino acid substitutions. A conservative amino acid substitution refers to the replacement of an amino acid by another which preserves the physicochemical character of the polypeptide (e.g. D may be replaced by E or vice versa, N by Q, or L or I by V or vice versa). Thus, generally the substituting amino acid has similar properties, e.g. hydrophobicity, hydrophilicity, electronegativity, bulky side chains etc. to the amino acid being replaced. Isomers of the native L-amino acid e.g. D-amino acids may be incorporated.

Sequence identity may be determined by any suitable means known in the art, e.g. using the SWISS-PROT protein sequence databank using FASTA pep-cmp with a variable pamfactor, and gap creation penalty set at 12.0 and gap extension penalty set at 4.0, and a window of 2 amino acids. Other programs for determining amino acid sequence identity include the BestFit program of the Genetics Computer Group (GCG) Version 10 Software package from the University of Wisconsin. The program uses the local homology algorithm of Smith and Waterman with the default values: Gap creation penalty-8, Gap extension penalty=2, Average match=2.912, Average mismatch=-2.003.

Preferably said comparison is made over the full length of the sequence, but may be made over a smaller window of comparison, e.g. less than 100, 80 or 50 contiguous amino acids.

Preferably such sequence identity-related proteins (polypeptide variants) are functionally equivalent to the polypeptides which are set forth in the recited SEQ ID NOs. As referred to herein, "functional equivalence" refers to variants of the polypeptide (peptide ligase) of the invention discussed above that may show some reduced efficacy in the ligation reaction (e.g. lower yield of reaction, lower reaction rate or activity in a limited range of reaction conditions (e.g. narrower temperature range, such as 10-30° C. etc.)) relative to the parent molecule (i.e. the molecule with which it shows sequence homology), but preferably are as efficient or are more efficient.

A mutant or variant polypeptide of the invention with ligase or catalytic activity that is "equivalent" to the ligase or catalytic activity of a polypeptide comprising or consisting of an amino acid sequence as set forth in SEQ ID NO: 1 may have ligase or catalytic activity that is similar (i.e. comparable) to the ligase or catalytic activity of a polypeptide comprising or consisting of an amino acid sequence as set forth in SEQ ID NO: 1, i.e. such that the practical applications of the peptide ligase are not significantly affected, e.g. within a margin of experimental error. Thus, an equivalent ligase or catalytic activity means that the mutant or variant polypeptide of the invention is capable of promoting the formation of an isopeptide bond between the peptide tags of the invention with a similar reaction rate and/or yield of reaction to a polypeptide comprising or consisting of an amino acid sequence as set forth in SEQ ID NO: 1 under the same conditions.

The ligase or catalytic activity of different peptide ligase polypeptides (e.g. SEQ ID NO: 1 versus mutant) measured under the same reaction conditions, e.g. temperature, substrates (i.e. peptide tag sequences) and their concentration, buffer, salt etc. as exemplified above, can be readily compared to determine whether the ligase or catalytic activity for each protein is higher, lower or equivalent.

Thus, the ligase or catalytic activity of the variant (e.g. mutant) polypeptide may be at least 60%, e.g. at least 70, 75, 80, 85 or 90% of the ligase or catalytic activity of a polypeptide comprising or consisting of an amino acid sequence as set forth in SEQ ID NO: 1, such as at least 91, 92, 93, 94, 95, 96, 97, 98 or 99% of the ligase or catalytic activity of a polypeptide comprising or consisting of an amino acid sequence as set forth in SEQ ID NO: 1. Alternatively viewed, the ligase or catalytic activity of the mutant polypeptide may be no more than 40% lower than the ligase or catalytic activity of a polypeptide comprising or consisting of an amino acid sequence as set forth in SEQ ID NO: 1, e.g. no more than 35, 30, 25 or 20% lower than the ligase or catalytic activity of a polypeptide comprising or consisting of an amino acid sequence as set forth in SEQ ID NO: 1, such as no more than 10, 9, 8, 7, 6, 5, 4, 3, 2 or 1% lower than the ligase or catalytic activity of a polypeptide comprising or consisting of an amino acid sequence as set forth in SEQ ID NO: 1.

In some embodiments, the ligase or catalytic activity of the variant (e.g. mutant) polypeptide may be assessed by measuring the yield of reaction of the peptide tags. The yield of reaction is measured by determining the proportion of a tag (e.g. SEQ ID NO: 2) in covalent complex with its partner peptide tag (e.g. SEQ ID NO: 3) relative to unreacted components following contact of the peptide tags with the polypeptide (peptide ligase) of the invention under conditions suitable for the formation of an isopeptide bond between said peptide tags and/or suitable for the ligase activity of the polypeptide of the invention. Thus, the yield of reaction refers to: the proportion of a tag (e.g. SEQ ID NO: 2) in covalent complex with its partner peptide tag (e.g. SEQ ID NO: 3)/(the proportion of the tag (e.g. SEQ ID NO: 2) in covalent complex with its partner peptide tag (e.g. SEQ ID NO: 3)+ the proportion of the tag (e.g. SEQ ID NO: 2) not in covalent complex with its partner peptide tag (e.g. SEQ ID NO: 3))×100.

As mentioned above, the peptide ligase comprising an amino acid sequence as set forth in SEQ ID NO: 1 is capable of catalysing the reaction of SEQ ID NO: 2 and SEQ ID NO: 3 with a yield of reaction of about 95%. Thus, in some embodiments a variant polypeptide of the invention that is functionally equivalent to a polypeptide comprising an amino acid sequence as set forth in SEQ ID NO: 1 is capable of catalysing the reaction of SEQ ID NO: 2 and SEQ ID NO: 3 (i.e. the formation of an isopeptide bond between SEQ ID NO: 2 and SEQ ID NO: 3) with a yield of reaction of at least about 57% e.g. a yield of reaction of at least about 67, 71, 76, 81 or 86%, such as at least 86.5, 87.4, 88.4, 89.3, 90.3, 91.2, 92.2, 93.1 or 94%.

Hence, any modification or combination of modifications may be made to SEQ ID NO: 1 to produce a variant polypeptide (peptide ligase) of the invention, provided that the variant polypeptide comprises a glutamic acid residue at a position equivalent to position 61 of SEQ ID NO: 1 and at least one (preferably 2, 3 or 4) other amino acid residue(s) at positions equivalent to positions 66, 95, 96 and 97 of SEQ ID NO: 1 as defined above and retains the functional characteristics defined above, i.e. it results in a peptide ligase capable of promoting the formation of an isopeptide bond between the peptide tags of the invention and optionally has an equivalent or higher yield of reaction, reaction rate, temperature and/or buffer range relative to a polypeptide having an amino acid sequence as set forth in SEQ ID NO: 1.

An equivalent position is determined by reference to the amino acid sequence of SEQ ID NO: 1. The homologous or corresponding position can be readily deduced by lining up the sequence of the homologue (mutant, variant or derivative) polypeptide and the sequence of SEQ ID NO: 1 based on the homology or identity between the sequences, for example using a BLAST algorithm.

As discussed above, the C-terminal domain of the *Streptococcus pneumoniae* adhesion protein, RrgA, was split into three domains, each of which was then modified to generate the polypeptide (peptide ligase) of the invention and two peptide tags. Thus, the peptide tags of the invention find particular utility in combination with the peptide ligase of the invention. Accordingly, the peptide tags of the invention may be viewed as substrates of the peptide ligase of the invention in a peptide ligation or conjugation reaction. Notably, the polypeptide ligase of the invention is able to direct a specific transamidation between the lysine residue at position 9 of SEQ ID NO: 2 and the asparagine residue at position 17 of SEQ ID NO: 3. Thus, the peptide tags of the invention may be viewed as substrates of the peptide ligase of the invention in a transamidation reaction.

Accordingly, in a further aspect, the invention provides a peptide tag comprising an amino acid sequence as set forth in SEQ ID NO: 2 or SEQ ID NO: 3.

The term "peptide tag" or "peptide linker" as used herein generally refers to a peptide or oligopeptide. There is no standard definition regarding the size boundaries between what is meant by peptide or oligopeptide but typically a peptide may be viewed as comprising between 2-20 amino acids and oligopeptide between 21-39 amino acids. Accordingly, a polypeptide may be viewed as comprising at least 40 amino acids, preferably at least 50, 60, 70 or 80 amino acids. Thus, a peptide tag or linker as defined herein may be viewed as comprising at least 12 amino acids, e.g. 12-39 amino acids, such as e.g. 13-35, 14-34, 15-33, 16-31, 17-30 amino acids in length, e.g. it may comprise or consist of 12, 13, 14, 15, 16, 17, 18, 19, 20, 21, 22 or 23 amino acids.

As discussed above, peptide tags have a large number of utilities and the peptide tags and peptide ligase of the invention find particular utility in conjugating (i.e. joining or linking) two molecules or components via an isopeptide bond. For instance, the peptide tags may be separately conjugated or fused to molecules or components of interest and subsequently contacted together in the presence of the peptide ligase under conditions suitable to allow the formation of an isopeptide bond between the peptide tags, thereby joining (i.e. linking or conjugating) the molecules or components via an isopeptide bond.

As shown in the Examples below, the inventors have determined that the peptide ligase of the invention binds strongly to its reaction product, i.e. the two peptide tags of the invention joined by an isopeptide bond and any molecules or components fused or conjugated to said peptide tags. However, the strong interaction may be disrupted using a variety of selected conditions, e.g. low pH, increased temperature (e.g. 45° C. or higher), addition of imidazole or a peptide competitor, or a combination thereof. Thus, in some embodiments, the strong interaction between the peptide ligase and its reaction product advantageously facilitates efficient purification of the reaction product.

By way of example, the peptide ligase of the invention may be immobilised on a solid support or solid phase by any convenient means, as discussed in more detail below, e.g. by labelling the peptide ligase with a tag, e.g. biotin, and contacting the tagged ligase with a solid support linked to the binding partner of the tag, e.g. streptavidin agarose. The solid support or solid phase is then contacted with molecules or components fused or conjugated to the peptide tags under conditions that allow the peptide ligase-mediated formation of an isopeptide bond between the peptide tags, thereby forming a covalent complex between the molecules or components. Due to the strong interaction between the immobilised peptide ligase and the reaction product, the solid phase may be washed under stringent conditions to facilitate the removal of non-reacted components. The solid phase is then subjected to conditions that disrupt the interaction between the immobilised peptide ligase and the reaction product, thereby allowing separation of the reaction product.

For instance, the solid phase may be contacted with a low pH solution, e.g. low pH buffer, such as a buffer with a pH of 4.0 or less, to disrupt the interaction between the immobilised peptide ligase and the reaction product, thereby allowing separation of the reaction product. For instance, the solid phase may be a column and contacting the column with a low pH solution results in the elution of a substantially pure reaction product.

As discussed below, one or more of the molecules or components to be conjugated via the peptide tags of the invention may be a protein. However, not all proteins tolerate treatment with low pH. Accordingly, the inventors sought to identify other conditions that allow separation of the peptide ligase and its reaction product at neutral pH (i.e. 6.5-7.5).

The inventors determined that elevating the temperature of the solid phase to 55° C. was sufficient to efficiently elute the reaction product under conditions that are tolerated by most proteins, e.g. in phosphate-buffered saline, pH 7.4.

Moreover, the inventors determined that efficient elution can be achieved at a lower temperature by adding competitor reaction product (e.g. pre-ligated protein) to disrupt (compete out) the non-covalent interaction between the reaction product and the peptide ligase. A competitor reaction product may be any product comprising the peptide tags of the invention that is easily separable from the intended reaction product (e.g. by dialysis or size-exclusion chromatography).

As shown in the Examples, the addition of 35 µM competitor reaction product (i.e. a competitor protein comprising a peptide tag (SEQ ID NO: 9) coupled to an AffiHER2-peptide tag (SEQ ID NO: 7) fusion using biotinylated SnoopLigase, subsequently purified by elution from a solid phase using a glycine buffer, pH 2) allowed efficient elution of the reaction product at 45° C. instead of 55° C. In a preferred embodiment, the competitor reaction product comprises or consists of a peptide having an amino acid sequence as set forth in SEQ ID NO: 2 ligated (via an isopeptide bond) to a peptide having an amino acid sequence as set forth in SEQ ID NO: 3. In some embodiments, the competitor reaction product is contacted with the solid phase at a high concentration, i.e. at least 60%, e.g. at least 70, 80, 90, 100, 110, 120, 130, 140, 150 or 200%, of the concentration of the reactants (i.e. peptide tag conjugates) used in the reaction. In particularly preferred embodiments, the competitor reaction product is contacted with the solid phase at an elevated temperature, i.e. above room temperature, e.g. at least 30, 35, 40 or 45° C.

Whilst the use of a competitor reaction product may be suitable for the elution of some reaction products (e.g. protein conjugates) from the peptide ligase of the invention, it is desirable to be able to disrupt the interaction between the peptide ligase of the invention and the reaction product under physiologically relevant conditions, e.g. physiological temperatures and pH. Accordingly, as discussed in the Examples, the inventors skilfully selected a range of additives that may be effective at disrupting the interaction between the peptide ligase of the invention and the reaction product under physiological conditions, while still being compatible with most proteins ligated by SnoopLigase maintaining their folded structure.

Of the twelve additives tested, only one additive (1 M imidazole) was found to be effective under physiological conditions (pH 6.5-7.0, 37° C.) and it was surprisingly determined that higher concentrations of imidazole (2 M) enable efficient elution at lower temperatures (25° C.).

Imidazole is well tolerated by most proteins, being used in one of the most common protein purification methods, to purify histidine-tagged proteins from Ni-NTA resin.

Thus, in some embodiments the solid phase may be contacted with a solution comprising imidazole, e.g. at a concentration of at least 1 M, preferably about 2 M, to disrupt the interaction between the immobilised peptide ligase and the reaction product. In particularly preferred embodiments, the solid phase is contacted with a solution comprising about 2 M imidazole at pH 6.5-7.5 (preferably about pH 7.0), at about 20-30° C. (preferably about 25° C.).

Whilst it may be useful to immobilise the peptide ligase on a solid support prior to contact with the peptide tags of the invention, it will be evident that this is not essential. For instance, the ligation reaction may take place in solution, which is subsequently applied to a solid support or solid phase, e.g. column, to separate the reaction product and peptide ligase. In some embodiments, the peptide ligase-reaction product complex may be applied to the solid phase under conditions suitable to immobilise the complex on the solid phase, either via the reaction product or peptide ligase, washed under suitable conditions and subsequently subjected to one or more of the conditions mentioned above, e.g. contacted with a low pH solution or solution comprising imidazole, to disrupt the complex, thereby separating the reaction product and peptide ligase. Alternatively, the peptide ligase-reaction product complex may be subjected to one or more of the conditions mentioned above in solution, e.g. contacted with a low pH solution, a solution comprising imidazole or a competitor reaction product, and subsequently separated by any suitable means, e.g. by contact with a solid phase with affinity to the reaction product or peptide ligase, size exclusion chromatography, dialysis etc.

Whilst the use of a solid support or solid phase is advantageous to generate a substantially pure reaction product, it will be evident that this is not essential. For instance, the ligation reaction may take place in solution and the peptide ligase-reaction product complex may be separated by degradation of the peptide ligase. For instance, the peptide ligase of the invention may be modified to insert a cleavage domain, such that cleavage of the cleavage domain, e.g. using a protease, is sufficient to disrupt the interaction between the peptide ligase and reaction product. The degraded peptide ligase may be subsequently separated from the reaction product using any suitable means known in the art.

In other embodiments, the strong interaction between the peptide ligase and its reaction product may be used to produce a complex between molecules or components fused or conjugated to the peptide tags and a molecule or component fused or conjugated to the peptide ligase. In this respect, the molecules or components fused or conjugated to the peptide tags are joined via an isopeptide bond to produce a reaction product as described above, which interacts non-covalently with the molecule or component fused or conjugated to the peptide ligase, thereby producing a complex of three molecules or components, wherein two of the molecules or components are linked via an isopeptide bond.

Thus, in some embodiments, the invention may be seen to provide the use of a polypeptide (peptide ligase) as defined herein to:
(1) conjugate two molecules or components via an isopeptide bond; or
(2) produce a complex between three molecules or components, wherein two of the molecules or components in the complex are conjugated via an isopeptide bond,
wherein said molecules or components conjugated via an isopeptide bond comprise:
a) a first molecule or component comprising a peptide tag comprising:
  (i) an amino acid sequence as set forth in SEQ ID NO: 2; or
  (ii) an amino acid sequence with at least 80% sequence identity to a sequence as set forth in SEQ ID NO: 2, wherein said amino acid sequence comprises a lysine residue at the position equivalent to position 9 of SEQ ID NO: 2; and
b) a second molecule comprising a peptide tag comprising:
  (i) an amino acid sequence as set forth in SEQ ID NO: 3; or
  (ii) an amino acid sequence with at least 80% sequence identity to a sequence as set forth in SEQ ID NO: 3, wherein said amino acid sequence comprises an asparagine residue at the position equivalent to position 17 of SEQ ID NO: 3, and
wherein the third molecule or component in the complex in (2) comprises a polypeptide (peptide ligase) of the invention as defined above.

In view of the comments above, it is evident that the third molecule or component in the complex in (2) interacts or binds non-covalently to the molecules or components in the complex that are conjugated via an isopeptide bond. In particular, the non-covalent interaction between the third molecule or component in the complex and the molecules or components in the complex that are conjugated via an isopeptide bond is mediated by (arises from or is via) the interaction between the peptide ligase and the conjugated peptide tags of the invention.

Alternatively viewed, the invention provides a process for conjugating two molecules or components via an isopeptide bond comprising:
a) providing a first molecule or component comprising a peptide tag comprising:
  (i) an amino acid sequence as set forth in SEQ ID NO: 2; or
  (ii) an amino acid sequence with at least 80% sequence identity to a sequence as set forth in SEQ ID NO: 2, wherein said amino acid sequence comprises a lysine residue at the position equivalent to position 9 of SEQ ID NO: 2;
b) providing a second molecule or component comprising a peptide tag comprising:
  (i) an amino acid sequence as set forth in SEQ ID NO: 3; or
  (ii) an amino acid sequence with at least 80% sequence identity to a sequence as set forth in SEQ ID NO: 3, wherein said amino acid sequence comprises an asparagine residue at the position equivalent to position 17 of SEQ ID NO: 3;
c) contacting said first and second molecules or components with a polypeptide (peptide ligase) of the invention, preferably wherein said polypeptide is immobilised on a solid substrate, under conditions that enable the formation of an isopeptide bond between the lysine residue at the position equivalent to position 9 of SEQ ID NO: 2 and the asparagine residue at the position equivalent to position 17 of SEQ ID NO: 3, thereby conjugating said first molecule to said second molecule via an isopeptide to form a complex.

In some embodiments, the polypeptide (peptide ligase) of the invention is conjugated or fused to a molecule or component to provide a third molecule or component and step c) results in the formation of a complex comprising three molecules or components, wherein the third molecule or component in the complex interacts or binds non-covalently to the first and second molecules or components in the complex that are conjugated via an isopeptide bond. In particular, the non-covalent interaction between the third molecule or component in the complex and the first and second molecules or components in the complex that are conjugated via an isopeptide bond is mediated by (arises from or is via) the interaction between the peptide ligase and the conjugated peptide tags of the invention.

In some embodiments when the polypeptide is immobilised on a solid substrate, the process comprises a further step of separating the complex (comprising only the first and second molecules or components conjugated via an isopeptide bond) from the solid substrate, wherein said step comprises subjecting the complex to conditions suitable to disrupt the complex, i.e. to disrupt the non-covalent interaction between the polypeptide and the reaction product.

In some embodiments, as mentioned above, conditions suitable to disrupt the complex comprise contacting said complex with a low pH solution or buffer. In some embodiments, conditions suitable to disrupt the complex comprise subjecting said complex to elevated temperatures, e.g. at least 30, 35, 40 or 45° C., such as 30-65, 35-60, 40-55° C., and/or contacting said complex with a solution comprising imidazole (e.g. at least 1 M, e.g. 1-4 M, 1-3 M or 1.5-2.5 M, preferably about 2 M imidazole) or a solution comprising a competitor reaction product (e.g. a high concentration of a competitor reaction product as defined above).

In still further embodiments, the process comprises a step of washing the solid substrate with a buffer prior to separating said complex from the solid substrate. It will be evident that any suitable buffer may be selected based on the molecules or components fused to the peptide tags. Furthermore, the step of washing the solid substrate may be repeated multiple times, e.g. 2, 3, 4, 5 or more times. Alternatively viewed, in some embodiments the process comprises multiple wash steps, wherein the same or different washing conditions may be used in each step.

As mentioned above, in some embodiments, the solid substrate is subjected to stringent washing conditions. The nature of the stringent washing conditions will depend on the molecules or components fused to the peptide tags and/or the composition of the solid substrate. The skilled person could select such conditions as a matter of routine. However, by way of example, stringent washing conditions may comprise washing with a solution comprising 50 mM glycine and 300 mM NaCl (pH 3.0) followed by a solution comprising 50 mM glycine (pH 3.0), wherein each wash may be repeated.

A "low pH solution or buffer" may be viewed as any solution or buffer suitable for disrupting the non-covalent interaction between the peptide ligase of the invention and its reaction product, i.e. the peptide tags of the invention conjugated via an isopeptide bond. In some embodiments, the low pH solution or buffer is an antibody elution buffer. In this respect, it is evident that the pH of the solution necessary to disrupt the interaction between the peptide ligase of the invention and its reaction product may depend on the components in the solution. By way of example, antibody elution buffers may comprise or consist of 50 mM glycine pH 2.2-2.8 or 100 mM citric acid buffer pH 3.5-4.0. Thus, in some embodiments, the low pH solution or buffer has a pH of 4.0 or less, e.g. 3.9, 3.8, 3.7, 3.6, 3.5, 3.4, 3.3, 3.2, 3.1, 3.0 or less, e.g. about 1.5-3.5, 1.6-3.4, 1.7-3.3, 1.8-3.2, 1.9-3.1 or 2.0-3.0, such as about 2.2-2.8 or 2.5-2.7.

The terms "conjugating" or "linking" in the context of the present invention with respect to connecting two or more molecules or components to form a complex refers to joining or conjugating said molecules or components, e.g. proteins, via a covalent bond, particularly an isopeptide bond which forms between the peptide tags that are incorporated in, or fused to, said molecules or components, e.g. proteins (e.g. peptide tags that form domains of said proteins).

In some embodiments, said peptide tag sequence above is at least 85, 90, 95, 96, 97, 98, 99 or 100% identical to the sequence (SEQ ID NOs: 2 or 3) to which it is compared.

Preferably such sequence identity-related peptide tags are functionally equivalent to the peptide tags which are set forth in the recited SEQ ID NOs. As discussed above, "functional equivalence" refers to homologues of the peptide tags discussed above that may show some reduced efficacy in forming isopeptide bonds with their respective partner, mediated by the peptide ligase of the invention, relative to the exemplified peptide tag (i.e. SEQ ID NO: 2 or 3, the molecule with which it shows sequence homology), but preferably are as efficient or are more efficient.

Thus, the capability of a mutant peptide tag for forming an isopeptide bond with its respective partner, mediated by the peptide ligase of the invention, may be at least 60%, e.g. at least 70, 75, 80, 85 or 90% of the capability of a peptide tag comprising or consisting of an amino acid sequence as set forth in SEQ ID NO: 2 or 3, such as at least 91, 92, 93, 94, 95, 96, 97, 98 or 99% of the capability of a peptide tag comprising or consisting of an amino acid sequence as set forth in SEQ ID NO: 2 or 3. Alternatively viewed, capability of a mutant peptide tag for forming an isopeptide bond with its respective partner, mediated by the peptide ligase of the invention, may be no more than 40% lower than the capability of a peptide tag comprising or consisting of an amino acid sequence as set forth in SEQ ID NO: 2 or 3, e.g. no more than 35, 30, 25 or 20% lower than the capability of a peptide tag comprising or consisting of an amino acid sequence as set forth in SEQ ID NO: 2 or 3, such as no more than 10, 9, 8, 7, 6, 5, 4, 3, 2 or 1% lower than the capability of a peptide tag comprising or consisting of an amino acid sequence as set forth in SEQ ID NO: 2 or 3.

Thus, for instance, a peptide tag comprising an amino acid sequence with at least 80% sequence identity to a sequence as set forth in SEQ ID NO: 2, wherein said amino acid sequence comprises a lysine residue at the position equivalent to position 9 of SEQ ID NO: 2, must be capable of forming an isopeptide bond with a peptide tag comprising an amino acid sequence as set forth in SEQ ID NO: 3, preferably with at least 60% of the reaction efficacy (e.g. yield, reaction rate etc.) as a peptide tag comprising an amino acid sequence as set forth in SEQ ID NO: 2.

Similarly, a peptide tag comprising an amino acid sequence with at least 80% sequence identity to a sequence as set forth in SEQ ID NO: 3, wherein said amino acid sequence comprises an asparagine residue at the position equivalent to position 17 of SEQ ID NO: 3, must be capable of forming an isopeptide bond with a peptide tag comprising an amino acid sequence as set forth in SEQ ID NO: 2, preferably with at least 60% of the reaction efficacy (e.g.

yield, reaction rate etc.) as a peptide tag comprising an amino acid sequence as set forth in SEQ ID NO: 3.

The definitions of the polypeptide variants of the invention described above, i.e. in relation to substitutions, deletions and insertions, are equally applicable to the peptide tag variants described above in the context of the uses and processes of the invention.

Hence, any modification or combination of modifications may be made to SEQ ID NO: 2 or 3 to produce a variant peptide tag for use in the invention, provided that the variant peptide tag comprises a lysine residue at a position equivalent to position 9 of SEQ ID NO: 2 or an asparagine residue at a position equivalent to position 17 of SEQ ID NO: 3 and retains the functional characteristics defined above, i.e. it results in a peptide tag capable of forming an isopeptide bond with its respective partner mediated by the peptide ligase of the invention under suitable conditions.

An equivalent position in the peptide tags is determined by reference to the amino acid sequence of SEQ ID NO: 2 or 3. The homologous or corresponding position can be readily deduced by lining up the sequence of the homologue (mutant, variant or derivative) peptide tag and the sequence of SEQ ID NO: 2 or 3 based on the homology or identity between the sequences, for example using a BLAST algorithm.

As mentioned above, in some embodiments, the peptide tags of the invention are fused or conjugated to other molecules or to other components or entities. Such molecules or components (i.e. entities) may be a nucleic acid molecule, protein, peptide, small-molecule organic compound, fluorophore, metal-ligand complex, polysaccharide, nanoparticle, nanotube, polymer, cell, virus, virus-like particle or any combination of these. In some embodiments the component or entity to which the peptide tag is fused or conjugated is a solid support, i.e. solid substrate or phase, as defined below.

Thus, alternatively viewed, the invention provides a nucleic acid molecule, protein, peptide, small-molecule organic compound, fluorophore, metal-ligand complex, polysaccharide, nanoparticle, nanotube, polymer, cell, virus, virus-like particle or any combination thereof or solid support fused or conjugated to a peptide tag of the invention.

The cell may be a prokaryotic or eukaryotic cell. In some embodiments the cell is a prokaryotic cell, e.g. a bacterial cell.

In some embodiments, the peptide tag may be conjugated or fused to a compound or molecule which has a therapeutic or prophylactic effect, e.g. an antibiotic, antiviral, vaccine, antitumour agent, e.g. a radioactive compound or isotope, cytokines, toxins, oligonucleotides and nucleic acids encoding genes or nucleic acid vaccines.

In some embodiments, the peptide tag may be conjugated or fused to a label, e.g. a radiolabel, a fluorescent label, luminescent label, a chromophore label as well as to substances and enzymes which generate a detectable substrate, e.g. horse radish peroxidase, luciferase or alkaline phosphatase. This detection may be applied in numerous assays where antibodies are conventionally used, including Western blotting/immunoblotting, histochemistry, enzyme-linked immunosorbent assay (ELISA), or flow cytometry (FACS) formats. Labels for magnetic resonance imaging, positron emission tomography probes and boron 10 for neutron capture therapy may also be conjugated to the peptide tag of the invention. Particularly, the peptide tag may be fused or produced with another peptide, for example His6 tag, and/or may be fused or produced with another protein, for example with the purpose of enhancing recombinant protein expression by fusing to Maltose Binding Protein.

In a particularly useful embodiment, the peptide tag and/or peptide ligase is fused or conjugated with another peptide, oligopeptide or polypeptide. For instance, the peptide tag may be produced as part of another peptide, oligopeptide or polypeptide using recombinant techniques as discussed below, i.e. as a recombinant or synthetic protein or polypeptide.

It will be evident that the peptide tag and/or peptide ligase of the invention based be fused to any protein or polypeptide. The protein may be derived or obtained from any suitable source. For instance, the protein may be in vitro translated or purified from biological and clinical samples, e.g. any cell or tissue sample of an organism (eukaryotic, prokaryotic), or any body fluid or preparation derived therefrom, as well as samples such as cell cultures, cell preparations, cell lysates etc. Proteins may be derived or obtained, e.g. purified from environmental samples, e.g. soil and water samples or food samples are also included. The samples may be freshly prepared or they may be prior-treated in any convenient way e.g. for storage.

As noted above, in a preferred embodiment, the protein may be produced recombinantly and thus the nucleic acid molecules encoding said proteins may be derived or obtained from any suitable source, e.g. any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa, viruses etc. In some embodiments, the proteins may be synthetic proteins. For example, the peptide and polypeptide (proteins) disclosed herein may be produced by chemical synthesis, such as solid-phase peptide synthesis.

The position of the peptide tag within a recombinant protein is not particularly important. Thus, in some embodiments the peptide tag may be located at the N-terminus or C-terminus of the recombinant or synthetic polypeptide. In some embodiments, the peptide tag may be located internally within the recombinant or synthetic polypeptide. Thus, in some embodiments the peptide tag may be viewed as an N-terminal, C-terminal or internal domain of the recombinant or synthetic polypeptide.

The peptide ligase is preferably located at the N-terminus or C-terminus of the recombinant or synthetic polypeptide. In some embodiments, the peptide ligase may be located internally within the recombinant or synthetic polypeptide. Thus, in some embodiments the peptide ligase may be viewed as an N-terminal, C-terminal or internal domain of the recombinant or synthetic polypeptide.

In some embodiments, it may be useful to include one or more spacers, e.g. a peptide spacer, between the peptide, oligopeptide or polypeptide to be joined or conjugated with peptide tag and/or peptide ligase. Thus, the peptide, oligopeptide or polypeptide and peptide tag and/or peptide ligase may be linked directly to each other or they may be linked indirectly by means of one or more spacer sequences. Thus, a spacer sequence may interspace or separate two or more individual parts of the recombinant or synthetic polypeptide. In some embodiments, a spacer may be N-terminal or C-terminal to the peptide tag and/or peptide ligase. In some embodiments, spacers may be at both sides of the peptide tag and/or peptide ligase.

The precise nature of the spacer sequence is not critical and it may be of variable length and/or sequence, for example it may have 1-40, more particularly 2-20, 1-15, 1-12, 1-10, 1-8, or 1-6 residues, e.g. 6, 7, 8, 9, 10 or more residues. By way of representative example the spacer sequence, if present, may have 1-15, 1-12, 1-10, 1-8 or 1-6 residues etc. The nature of the residues is not critical and they may for example be any amino acid, e.g. a neutral amino acid, or an aliphatic amino acid, or alternatively they may be hydrophobic, or polar or charged or structure-forming e.g. proline. In some preferred embodiments, the linker is a serine and/or glycine-rich sequence, preferably comprising at least 6 amino acid residues, e.g. 6, 7 or 8 residues.

Exemplary spacer sequences thus include any single amino acid residue, e.g. S, G, L, V, P, R, H, M, A or E or a di-, tri- tetra- penta- or hexa-peptide composed of one or more of such residues.

Thus, in some embodiments, the invention provides a recombinant or synthetic polypeptide comprising a peptide tag or peptide ligase of the invention as defined above, i.e. a recombinant or synthetic polypeptide comprising a peptide, oligopeptide or polypeptide fused to a peptide tag or peptide ligase of the invention. The recombinant or synthetic polypeptide optionally comprises a spacer as defined above.

The recombinant or synthetic polypeptide of the invention may also comprise purification moieties or tags to facilitate their purification (e.g. prior to use in the methods and uses of the invention discussed below). Any suitable purification moiety or tag may be incorporated into the polypeptide and such moieties are well known in the art. For instance, in some embodiments, the recombinant or synthetic polypeptide may comprise a peptide purification tag or moiety, e.g. a His-tag sequence. Such purification moieties or tags may be incorporated at any position within the polypeptide. In some preferred embodiments, the purification moiety is located at or towards (i.e. within 5, 10, 15, 20 amino acids of) the N- or C-terminus of the polypeptide.

As noted above, an advantage of the present invention arises from the fact that the peptide tags and/or peptide ligase incorporated in peptide, oligopeptides or polypeptide (e.g. the recombinant or synthetic polypeptides of the invention) may be completely genetically encoded. Thus, in a further aspect, the invention provides a nucleic acid molecule encoding a peptide tag, peptide ligase or recombinant or synthetic polypeptide as defined above.

In some embodiments, the nucleic acid molecule encoding a peptide tag defined above comprises a nucleotide sequence as set forth in any one of SEQ ID NOs: 6-7 or a nucleotide sequence with at least 80% sequence identity to a sequence as set forth in any one of SEQ ID NOs: 6-7.

In some embodiments, the nucleic acid molecule encoding a peptide ligase defined above comprises a nucleotide sequence as set forth in SEQ ID NO: 5 or a nucleotide sequence with at least 80% sequence identity to a sequence as set forth in SEQ ID NO:5.

Preferably, the nucleic acid molecule above is at least 85, 90, 95, 96, 97, 98, 99 or 100% identical to the sequence to which it is compared.

Nucleic acid sequence identity may be determined by, e.g. FASTA Search using GCG packages, with default values and a variable pamfactor, and gap creation penalty set at 12.0 and gap extension penalty set at 4.0 with a window of 6 nucleotides. Preferably said comparison is made over the full length of the sequence, but may be made over a smaller window of comparison, e.g. less than 600, 500, 400, 300, 200, 100 or 50 contiguous nucleotides.

The nucleic acid molecules of the invention may be made up of ribonucleotides and/or deoxyribonucleotides as well as synthetic residues, e.g. synthetic nucleotides, that are capable of participating in Watson-Crick type or analogous base pair interactions. Preferably, the nucleic acid molecule is DNA or RNA.

The nucleic acid molecules described above may be operatively linked to an expression control sequence, or a recombinant DNA cloning vehicle or vector containing such a recombinant DNA molecule. This allows intracellular expression of the peptides and polypeptides of the invention as a gene product, the expression of which is directed by the gene(s) introduced into cells of interest. Gene expression is directed from a promoter active in the cells of interest and may be inserted in any form of linear or circular nucleic acid (e.g. DNA) vector for incorporation in the genome or for independent replication or transient transfection/expression. Suitable transformation or transfection techniques are well described in the literature. Alternatively, the naked nucleic acid (e.g. DNA or RNA, which may include one or more synthetic residues, e.g. base analogues) molecule may be introduced directly into the cell for the production of peptides and polypeptides of the invention. Alternatively the nucleic acid may be converted to mRNA by in vitro transcription and the relevant proteins may be generated by in vitro translation.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Examples of suitable vectors include bacterial and mammalian expression vectors pGEX-KG, pEF-neo and pEF-HA.

As noted above, the recombinant or synthetic polypeptide of the invention may comprise additional sequences (e.g. peptide/polypeptides tags to facilitate purification of the polypeptide) and thus the nucleic acid molecule may conveniently be fused with DNA encoding an additional peptide or polypeptide, e.g. His-tag, maltose-binding protein, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting a nucleic acid molecule of the invention encoding the peptide tag and/or polypeptide of the invention into vector nucleic acid.

Nucleic acid molecules of the invention, preferably contained in a vector, may be introduced into a cell by any appropriate means. Suitable transformation or transfection techniques are well described in the literature. Numerous techniques are known and may be used to introduce such vectors into prokaryotic or eukaryotic cells for expression. Preferred host cells for this purpose include insect cell lines, yeast, mammalian cell lines or *E. coli*, such as strain BL21/DE3. The invention also extends to transformed or transfected prokaryotic or eukaryotic host cells containing a nucleic acid molecule, particularly a vector as defined above.

Thus, in another aspect, there is provided a recombinant host cell containing a nucleic acid molecule and/or vector as described above.

By "recombinant" is meant that the nucleic acid molecule and/or vector has been introduced into the host cell. The host cell may or may not naturally contain an endogenous copy of the nucleic acid molecule, but it is recombinant in that an exogenous or further endogenous copy of the nucleic acid molecule and/or vector has been introduced.

A further aspect of the invention provides a method of preparing a peptide tag and/or polypeptide of the invention as hereinbefore defined, which comprises culturing a host cell containing a nucleic acid molecule as defined above, under conditions whereby said nucleic acid molecule encoding said peptide tag and/or polypeptide is expressed and recovering said molecule (peptide tag and/or polypeptide) thus produced. The expressed peptide tag and/or polypeptide forms a further aspect of the invention.

In some embodiments, the peptide tags and/or polypeptides of the invention, or for use in the method and uses of the invention, may be generated synthetically, e.g. by ligation of amino acids or smaller synthetically generated peptides, or more conveniently by recombinant expression of a nucleic acid molecule encoding said polypeptide as described hereinbefore.

Nucleic acid molecules of the invention may be generated synthetically by any suitable means known in the art.

Thus, the peptide tag and/or polypeptide of the invention may be an isolated, purified, recombinant or synthesised peptide tag or polypeptide.

The term "polypeptide" is used herein interchangeably with the term "protein". As noted above, the term polypeptide or protein typically includes any amino acid sequence comprising at least 40 consecutive amino acid residues, e.g. at least 50, 60, 70, 80, 90, 100, 150 amino acids, such as 40-1000, 50-900, 60-800, 70-700, 80-600, 90-500, 100-400 amino acids.

Similarly, the nucleic acid molecules of the invention may be an isolated, purified, recombinant or synthesised nucleic acid molecule.

Thus, alternatively viewed, the peptide tags, polypeptides and nucleic acid molecules of the invention preferably are non-native, i.e. non-naturally occurring, molecules.

Standard amino acid nomenclature is used herein. Thus, the full name of an amino acid residue may be used interchangeably with one letter code or three letter abbreviations. For instance, lysine may be substituted with K or Lys, isoleucine may be substituted with I or Ile, and so on. Moreover, the terms aspartate and aspartic acid, and glutamate and glutamic acid are used interchangeably herein and may be replaced with Asp or D, or Glu or E, respectively.

Whilst it is envisaged that the peptide tags and polypeptides of, and for use in, the invention may be produced recombinantly, and this is a preferred embodiment of the invention, it will be evident that the peptide tags of the invention may be conjugated to proteins or other entities, e.g. molecules, as defined above by other means. In other words, the peptide tag and other molecule, component or entity, e.g. protein, may be produced separately by any suitable means, e.g. recombinantly, and subsequently conjugated (joined) to form a peptide tag-other component conjugate that can be used in the methods and uses of the invention. For instance, the peptide tags of the invention may be produced synthetically or recombinantly, as described above, and conjugated to another component, e.g. a protein via a non-peptide linker or spacer, e.g. a chemical linker or spacer.

Thus, in some embodiments, the peptide tag and other component, e.g. protein, may be joined together either directly through a bond or indirectly through a linking group. Where linking groups are employed, such groups may be chosen to provide for covalent attachment of the peptide tag and other entity, e.g. protein, through the linking group. Linking groups of interest may vary widely depending on the nature of the other entity, e.g. protein. The linking group, when present, is in many embodiments biologically inert.

A variety of linking groups are known to those of skill in the art and find use in the invention. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the peptide tag and other molecule or component, e.g. protein.

Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine, oligoethylene glycol and polyethylene glycol. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject blocking reagent include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like. For instance, a spacer may be formed with an azide reacting with alkyne or a tetrazine reacting with trans-cyclooctene or norbornene.

In some embodiments, it may be useful to modify one or more residues in the peptide tag and/or polypeptide to facilitate the conjugation of these molecules and/or to improve the stability of the peptide tag and/or polypeptide. Thus, in some embodiments, the peptide tag or polypeptide of, or for use in, the invention may comprise unnatural or non-standard amino acids.

In some embodiments, the peptide tag or polypeptide of, or for use in, the invention may comprise one or more, e.g. at least 1, 2, 3, 4, 5 non-conventional amino acids, such as 10, 15, 20 or more non-conventional, i.e. amino acids which possess a side chain that is not coded for by the standard genetic code, termed herein "non-coded amino acids" (see e.g. Table 1). These may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group.

Examples of non-standard or structural analogue amino acids which may be used in the peptide linkers or polypeptides of, and for use in, the invention are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional, i.e. non-coded, amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |

TABLE 1-continued

| Non-conventional amino acid | Code | Non-conventional amino acid | Code |
|---|---|---|---|
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhse |

As discussed above, in some embodiments, it may be useful to fuse or conjugate the peptide tag and/or polypeptide (peptide ligase) of the invention to a solid substrate (i.e. a solid phase or support) and it will be evident that this may be achieved in any convenient way. Thus the manner or means of immobilisation and the solid support may be selected, according to choice, from any number of immobilisation means and solid supports as are widely known in the art and described in the literature. Thus, the peptide tag and/or polypeptide may be directly bound to the support, for example via a domain or moiety of the peptide tag or polypeptide (e.g. chemically cross-linked). In some embodiments, the peptide tag or polypeptide may be bound indirectly by means of a linker group, or by an intermediary binding group(s) (e.g. by means of a biotin-streptavidin interaction). Thus, the peptide tag or polypeptide may be covalently or non-covalently linked to the solid support. The linkage may be a reversible (e.g. cleavable) or irreversible linkage. Thus, in some embodiments, the linkage may be cleaved enzymatically, chemically or with light, e.g. the linkage may be a light-sensitive linkage.

Thus, in some embodiments, a peptide tag or polypeptide may be provided with means for immobilisation (e.g. an affinity binding partner, e.g. biotin or a hapten, capable of binding to its binding partner, i.e. a cognate binding partner, e.g. streptavidin or an antibody) provided on the support. In some embodiments, the interaction between the peptide tag or polypeptide and the solid support must be robust enough to allow for washing steps, i.e. the interaction between the peptide tag or polypeptide and solid support is not disrupted (significantly disrupted) by the washing steps described above. For instance, it is preferred that with each washing step, less than 5%, preferably less than 4, 3, 2, 1, 0.5 or 0.1% of the peptide tag or polypeptide is removed or eluted from the solid phase.

The solid support (phase or substrate) may be any of the well-known supports or matrices which are currently widely used or proposed for immobilisation, separation etc. These may take the form of particles (e.g. beads which may be magnetic, para-magnetic or non-magnetic), sheets, gels, filters, membranes, fibres, capillaries, slides, arrays or microtitre strips, tubes, plates or wells etc.

The support may be made of glass, silica, latex or a polymeric material. Suitable are materials presenting a high surface area for binding of the fusion protein. Such supports may have an irregular surface and may be for example porous or particulate, e.g. particles, fibres, webs, sinters or sieves. Particulate materials, e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the isopeptide bond formation steps.

In some embodiments, the solid support is an agarose resin.

As discussed in the Examples, the inventors have surprisingly determined that the peptide ligase of the invention may be lyophilized without significant loss of activity. This may be particularly advantageous for long-term storage and/or shipping of the polypeptide at ambient temperatures, i.e. without the need for cooling. Thus, in some embodiments, the polypeptide (peptide ligase) and peptide tags of the invention may be in a lyophilized state. Alternatively viewed, the invention provides a lyophilized polypeptide (peptide ligase) as defined above. The invention may also provide lyophilized peptide tags as defined above. Lyophilization may be achieved using any suitable means known in the art.

In a further embodiment, the invention provides a kit, particularly a kit for use in the processes and uses of the invention, i.e. for conjugating two molecules or components via an isopeptide bond or for producing a complex between three molecules or components, wherein two of the molecules or components in the complex are conjugated via an isopeptide bond, wherein said kit comprises:

(a) a peptide ligase as defined above, optionally conjugated or fused to a molecule or component, e.g. a protein; and (b) a peptide tag comprising:

(i) an amino acid sequence as set forth in SEQ ID NO: 2;

(ii) an amino acid sequence with at least 80% sequence identity to a sequence as set forth in SEQ ID NO: 2, wherein said amino acid sequence comprises a lysine residue at the position equivalent to position 9 of SEQ ID NO: 2, (iii) an amino acid sequence as set forth in SEQ ID NO: 3; or (iv) an amino acid sequence with at least 80% sequence identity to a sequence as set forth in SEQ ID NO: 3, wherein said amino acid sequence comprises an asparagine residue at the position equivalent to position 17 of SEQ ID NO: 3, wherein said peptide tag is conjugated or fused to a molecule or component, e.g. a protein such as a recombinant or synthetic polypeptide comprising a peptide tag as defined above; and/or (c) a nucleic acid molecule, particularly a vector, encoding a peptide ligase as defined in (a); and (d) a nucleic acid molecule, particularly a vector, encoding a peptide tag as defined in (b).

In some embodiments the kit may further comprise a second peptide tag conjugated or fused to a molecule or component, e.g. a protein such as a recombinant or synthetic polypeptide comprising a peptide tag as defined above, wherein the second peptide tag is capable of forming an isopeptide bond with the peptide tag in (b) when contacted with a peptide ligase of (a) under conditions suitable for the formation of an isopeptide bond as defined above. Thus, in some embodiments, the kit comprises a peptide tag comprising an amino acid sequence as set forth in SEQ ID NO: 2 (or variant thereof) conjugated or fused to a molecule or component and an amino acid sequence as set forth in SEQ ID NO: 3 (or variant thereof) conjugated or fused to a molecule or component.

It will be evident that the peptide ligase and peptide tags of the invention have a wide range of utilities. Alternatively viewed, the peptide ligase and peptide tags of the invention may be employed in a variety of industries.

For instance, in some embodiments, the peptide ligase and peptide tags of the invention may find utility in targeting fluorescent or other biophysical probes or labels to specific proteins. In this respect, the protein of interest may be modified to incorporate a first peptide tag (e.g. SEQ ID NO: 2), as discussed above, and the fluorescent or other biophysical probe or label may be fused or conjugated to the second peptide tag (e.g. SEQ ID NO: 3). The modified protein and probe or label may be contacted together in the presence of the peptide ligase under conditions suitable to allow the formation of an isopeptide bond between the peptide tags, thereby labelling the protein with the label or probe via an isopeptide bond.

In some embodiments, the peptide ligase and peptide tags of the invention may find utility in protein immobilisation for proteomics. In this respect, the proteins of interest may be modified to incorporate a first peptide tag (e.g. SEQ ID NO: 2) and a solid substrate may be fused or conjugated to the second peptide tag (e.g. SEQ ID NO: 3). The modified proteins and solid substrate may be contacted together in the presence of the peptide ligase under conditions suitable to allow the formation of an isopeptide bond between the peptide tags, thereby immobilising the proteins on the solid substrate via an isopeptide bond. It will be evident that the peptide tags and ligase of the invention may be used to simultaneously immobilise multiple proteins on a solid phase/substrate.

In still further embodiments, the peptide ligase and peptide tags of the invention may find utility in conjugation of antigens to virus-like particles, viruses, bacteria or multimerisation scaffolds for vaccination. For instance, the production of virus-like particles, viruses or bacteria that display a first peptide tag on the surface would facilitate the conjugation of antigens comprising a second peptide tag to their surface via an isopeptide bond, using the peptide ligase of the invention to mediate the formation of the isopeptide bond. In this respect, antigen multimerisation gives rise to greatly enhanced immune responses. Thus, in some embodiments, the molecule or component fused to the first peptide of the invention is a viral capsid protein and/or the molecule or component fused to the second peptide tag of the invention is an antigen, e.g. an antigen associated with a particular disease, e.g. infection.

In other embodiments, the peptide tags may be used to cyclise or a protein, e.g. by fusing peptide tags to each end of the protein and subsequently contacting the protein with the peptide ligase of the invention to mediate or promote the formation of the isopeptide bond between the peptide tags. In this respect, cyclisation of proteins has been shown to increase protein resilience, e.g. to heat, organic solvent, extreme pH or proteolytic degradation.

In particular, cyclisation of enzymes or enzyme polymers (fusion proteins) may improve the thermostability of the protein or protein units in the enzyme polymer. In this respect, enzymes are valuable tools in many processes but are unstable and hard to recover. Enzyme polymers have greater stability to temperature, pH and organic solvents and there is an increased desire to use enzyme polymers in industrial processes. However, enzyme polymer generation commonly uses a glutaraldehyde non-specific reaction and this will damage or denature (i.e. reduce the activity of) many potentially useful enzymes. Site-specific linkage of proteins into chains (polymers) through isopeptide bonds using the peptide tags and peptide ligase of the present invention is expected to enhance enzyme resilience, such as in diagnostics or enzymes added to animal feed. In particularly preferred embodiments, enzymes may be stabilised by cyclisation, as discussed above.

The peptide ligase and peptide tags of the invention could also be used to link multiple enzymes into pathways to promote metabolic efficiency, as described in WO 2016/193746. In this respect, enzymes often come together to function in pathways inside cells and traditionally it has been difficult to connect multiple enzymes together outside cells (in vitro). Thus, the peptide tags and peptide ligase of the invention could be used to couple or conjugate enzymes to produce fusion proteins and therefore enhance activity of multi-step enzyme pathways, which could be useful in a range of industrial conversions and for diagnostics. For instance, the fusion protein can create signalling teams for inducing cellular responses, e.g. in differentiation or therapy.

The peptide tags and peptide ligase of the invention will also find utility in the production of antibody polymers. In this respect, antibodies are one of the most important classes of pharmaceuticals and are often used attached to surfaces. However, antigen mixing in a sample, and therefore capture of said antigen in said sample, are inefficient near surfaces. By extending chains of antibodies, it is anticipated that capture efficiency will be improved. This will be especially valuable in circulating tumour cell isolation, which at present is one of the most promising ways to enable early cancer diagnosis. Also antibodies of different specificities can be combined in any desired order.

In a still further embodiment, the peptide tags and peptide ligase of the invention may find utility in the production of drugs for activating cell signalling. In this respect, many of the most effective ways to activate cellular function are through protein ligands. However, in nature a protein ligand will usually not operate alone but with a specific combination of other signalling molecules. Thus, the peptide tags and peptide ligase of the invention allows the generation of tailored fusion proteins (i.e. protein teams), which could give optimal activation of cellular signalling. These fusion proteins (protein teams) might be applied for controlling cell survival, division, or differentiation.

In yet further embodiments, the peptide tags and peptide ligase of the invention may find utility in the generation of hydrogels for growth of stem cells, preparation of biomaterials, antibody functionalisation with dyes or enzymes and stabilising enzymes by cyclisation.

The invention will now be described in more detail in the following non-limiting Examples with reference to the following drawings:

FIG. 1 (A) shows a cartoon of how the RrgA was split and modified to arrive at the peptide tags and peptide ligase of the invention. The C-terminal domain of RrgA (Protein Data Bank 2WW8) was split into three parts and engineered, such that the reactive Lys is located on SnoopTagJr, the reactive Asn on DogTag and the catalytic Glu on SnoopLigase. (B) shows the molecular basis for isopeptide bond formation in RrgA, wherein Glu 803 catalyes isopeptide bond formation between Lys 742 and Asn 854, eliminating ammonia (Residue numbers as in PDB file). (C) shows a cartoon of the use of DogTag and SnoopTagJr for peptide-peptide ligation.

FIG. 2 (A) is a graph showing the reactivity of different RrgALigase mutants, wherein: RrgALigase refers to a polypeptide comprising a sequence as set forth in SEQ ID NO: 8; A808P refers to a polypeptide comprising a sequence as set forth in SEQ ID NO: 8, wherein residue 66 is proline; A808P Q837P refers to a polypeptide comprising a sequence as set forth in SEQ ID NO: 8, wherein residues 66 and 95 are both proline; A808P Q837P D838G refers to a polypeptide comprising a sequence as set forth in SEQ ID NO: 8, wherein residues 66 and 95 are both proline and residue 96 is glycine; and SnoopLigase refers to a polypeptide comprising a sequence as set forth in SEQ ID NO: 1. (B) a photograph of an SDS-PAGE gel with Coomassie staining characterising the SnoopLigase, SnoopTagJr and DogTag reactivity alongside controls with alanine mutation of SnoopTagJr's reactive Lys (KA) and DogTag's reactive Asn (NA) and glutamine mutation of SnoopLigase's reactive Glu (EQ), wherein SnoopTagJr was expressed as a fusion protein with an affibody to HER2 and DogTag was expressed as a fusion protein with SUMO.

EXAMPLES

Example 1

Development of the Peptide Ligase (SnoopLigase) and Peptide Tags

RrgA (SEQ ID NO: 4) is an adhesin from *Streptococcus pneumoniae*, a Gram-positive bacterium which can cause septicaemia, pneumonia and meningitis in humans. A spontaneous isopeptide bond forms in the D4 immunoglobulin-like domain of RrgA between residues Lys742 and Asn854.

The inventors "split" the D4 domain into a three parts, a pair of peptide tags termed SnoopTag (residues 734-745 of RrgA, SEQ ID NO: 9) and RrgATag2 (residues 838-860 of RrgA, SEQ ID NO:10) and a protein which was named RrgALigase (residues 743-846, SEQ ID NO: 8). Notably, there is an overlap of 9 amino acids between the N-terminus of RrgATag2 and the C-terminus of RrgALigase. Similarly, there is an overlap of 3 amino acids between the C-terminus of SnoopTag and the N-terminus of RrgALigase. Furthermore, the RrgALigase and RrgATag2 sequences incorporate modifications relative to the native RrgA sequence which are known to be important for promoting the reaction rate of the isopeptide bond formation. In particular, the glycine at position 842 of RrgA was substituted with threonine at the corresponding (equivalent) position in RrgALigase and RrgATag2. Moreover, the aspartic acid at position 848 of RrgA was substituted with glycine at the corresponding position in RrgATag2.

The selection of the sites at which to "split" the RrgA D4 domain was found to be important for the activity of the peptide ligase and peptide tags. In this respect, it is a general principle in the design of peptide tags that they should be as short as possible, so as to limit any unwanted interactions when incorporated in the molecules or components, e.g. proteins, to be linked together. Accordingly, the inclusion of sequences in peptide tags that overlap with the peptide ligase is not consistent with standard design principles. However, it was determined that the overlapping sequences are essential for the activity of the ligase and peptide tags, as removal of these sequences from the tags or ligase was found to significantly disrupt the efficacy of the ligation reaction. Whilst not wishing to be bound by theory, it is hypothesised that the presence of overlapping sequences improves the stability of the interaction between the peptide tags and ligase portions of the D4 domain of RrgA.

Figure 1:
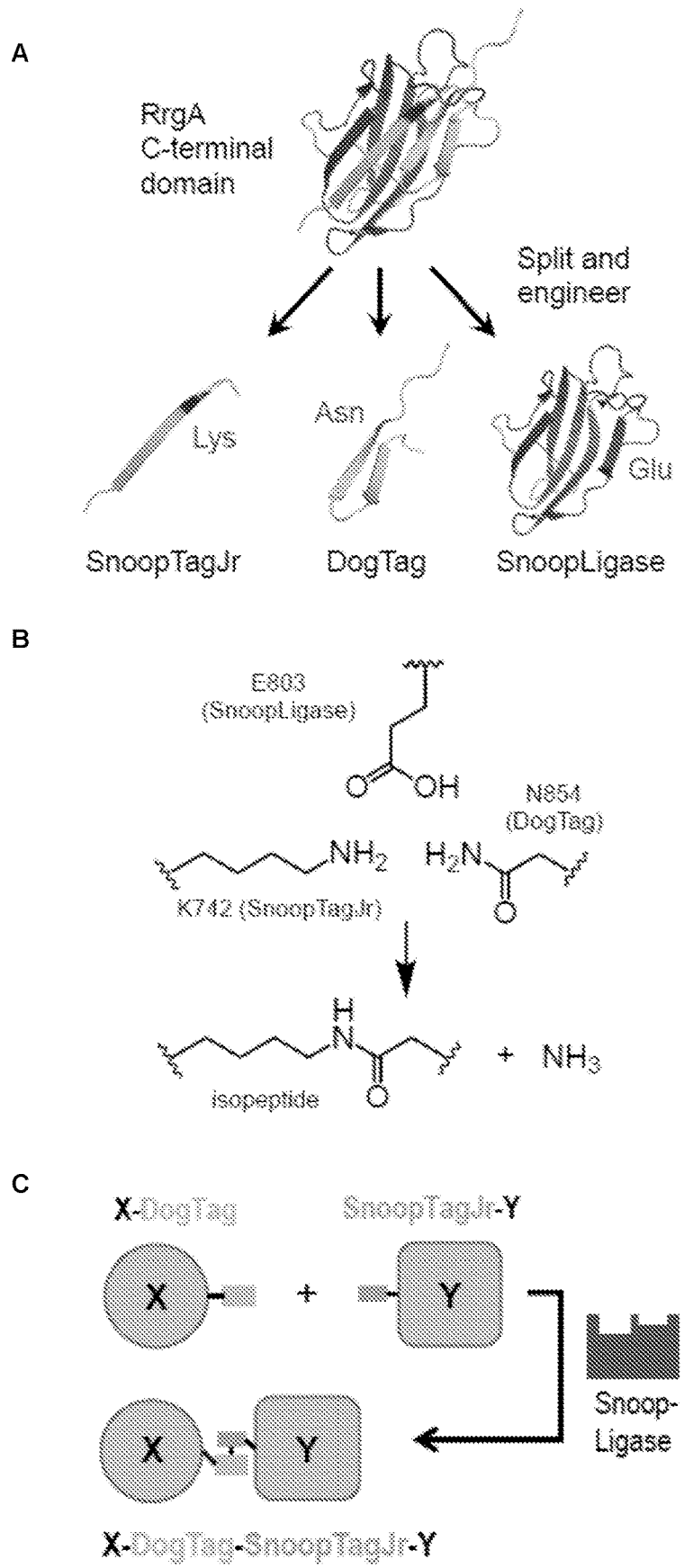
Figure 2:
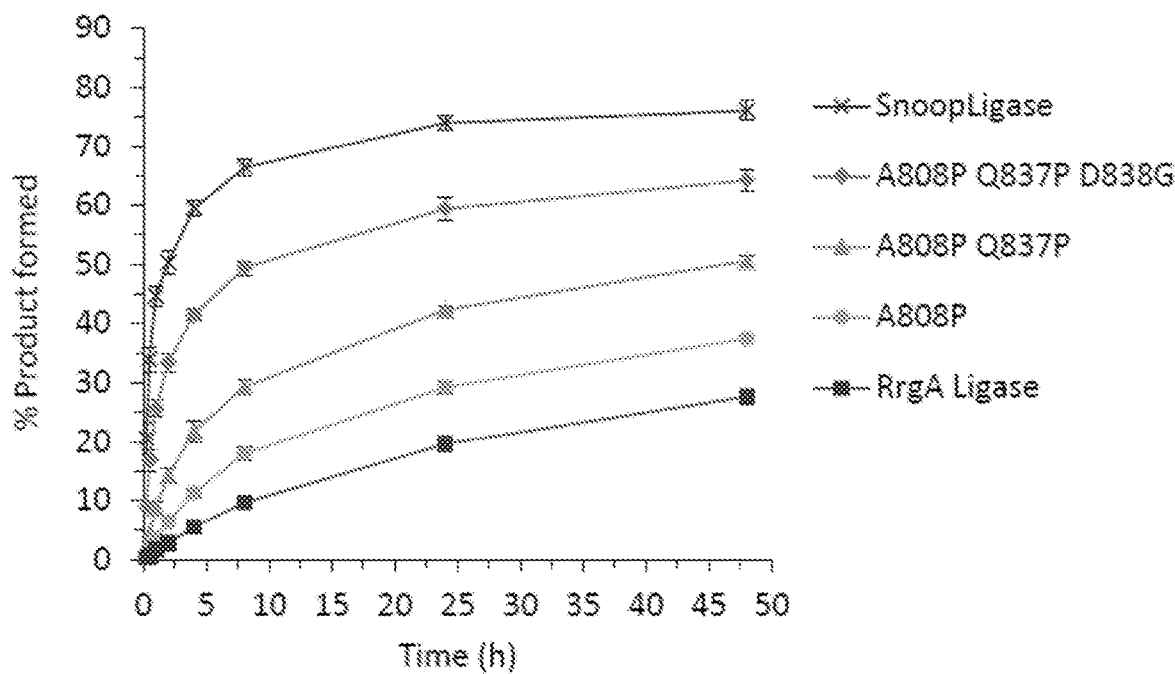
Figure 2:
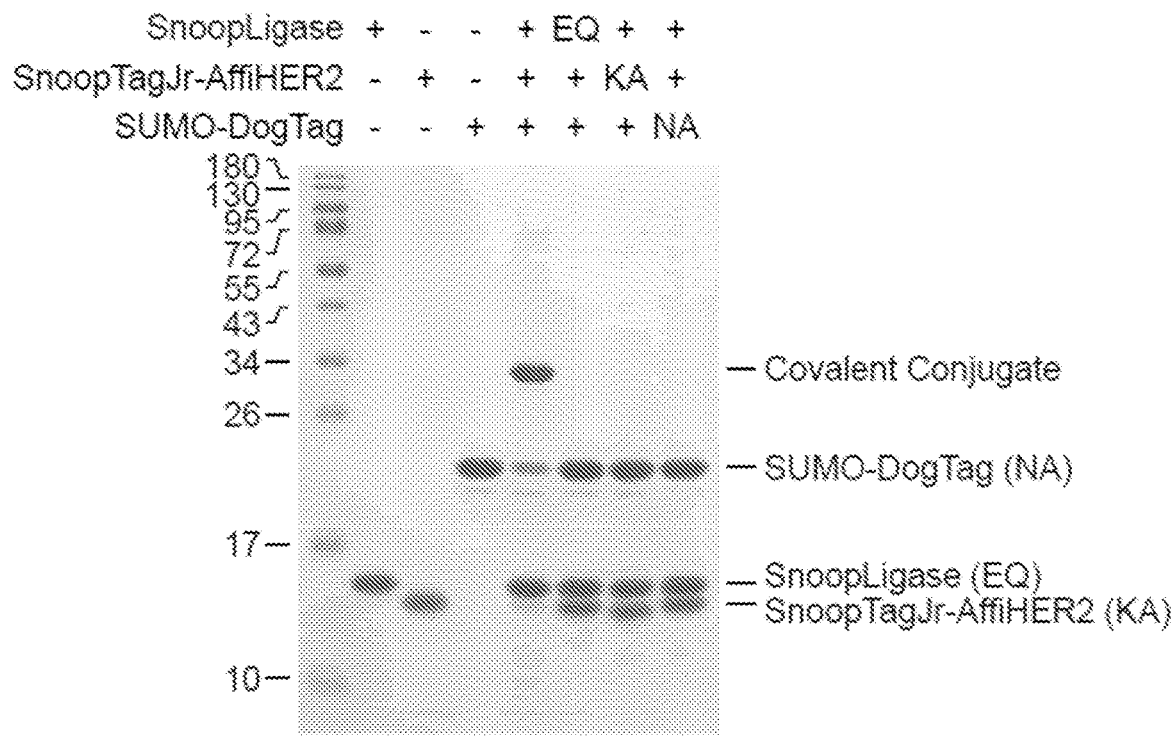

The N- and C-terminal sites selected for the RrgALigase protein resulted in removal of 3 β-strands, which is a major modification, particularly for a small protein, i.e. the D4 domain of RrgA. In this respect, the RrgALigase was shown to have poor solubility and limited ligase activity (see FIG. 2). Indeed, RrgALigase was shown to be insoluble in solutions comprising NaCl, such as Phosphate buffered saline (PBS), which severely limits its utility, particularly in cellular environments of living organisms. Moreover, many in vitro biological assays require the presence of NaCl.

Since RrgALigase was most active at 4° C., it was hypothesised that stabilising the split domains would be important to enhance ligase performance. To achieve this stabilisation, the inventors sought to engineer β-turns of the protein domain by substituting appropriate residues with proline. β-turns are flexible protein elements. Proline has a fixed φ-angle of −60° and thereby limits protein conformational flexibility.

The RrgALigase sequence was screened manually for sites suitable for mutation to proline based on the crystal structure. Twenty sites were identified and six were selected for modification. However, only two proline substitutions (A66P and Q95P, based on the numbering in SEQ ID NO: 8) were shown to improve activity, see FIG. 2.

It was hypothesised that the ligation reaction rate could be improved by further stabilizing the protein. Accordingly, the inventors analyzed the RrgA C-terminal domain using the Protein Repair One Stop Shop (PROSS). PROSS analyses proteins based on protein sequence homology and atomistic Rosetta modelling. However, the multiple sequence alignment (MSA) used by PROSS only identified 35 homologous sequences, which is insufficient to provide meaningful results. Accordingly, the inventors manually generated a separate MSA for RrgA to input into PROSS.

PROSS analysis suggested fifteen mutations that may improve the stability of the RrgA C-terminal domain and five were selected for further analysis (D737S, A820E, D830N, D838G and I839V based on the numbering in RrgA, SEQ ID NO: 4), based on structure-based inspection of potential contacts made by the newly introduced amino acid side-chains. Notably, one of the mutations identified in the PROSS analysis, D737S, was in the SnoopTag sequence. The engineered versions of SnoopTag and RrgALigase incorporating the aforementioned mutations were named SnoopTagJr (SEQ ID NO: 2) and SnoopLigase (SEQ ID NO: 1), respectively. Based on truncation studies of RrgA-Tag2, the inventors also hypothesised that mutation of the asparagine residue at position 847 of RrgA (position 10 of RrgATag2, SEQ ID NO: 10) to aspartic acid would also reduce the heterogeneity of peptide-tagged protein. The modified version of RrgATag2 was termed DogTag.

Some of the PROSS mutations in RrgALigase substantially improved reaction yield and rate (FIG. 2), but A820E and D830N did not improve the activity of the ligase. Similarly, the D737S mutation in SnoopTag (i.e. resulting in SnoopTagJr) also was very successful in improving reaction with DogTag.

In view of the poor solubility of RrgALigase, the protein was initially expressed as a maltose binding protein (MBP) fusion protein to reduce aggregation after expression and to facilitate analysis. However, it was surprisingly found that when SnoopLigase was produced without MBP fusion, SnoopLigase's solubility was improved relative to RrgALigase. SnoopLigase was expressed efficiently in *E. coli* (>10 mg per litre of culture) and was highly soluble (>500 μM). As discussed below in Example 3, SnoopLigase is active in a variety of conditions, including at physiological extracellular concentrations of NaCl. Thus, mutation of RrgALigase (SEQ ID NO: 8) to generate SnoopLigase (SEQ ID NO: 1) also improved the solubility of the protein.

To validate the proposed mechanism of reaction and the specificity of residue ligation by SnoopLigase, the reaction was analysed by SDS-PAGE with each of the key residues mutated. SnoopLigase efficiently ligated an affibody fused with SnoopTagJr to a SUMO domain fused to DogTag. However, mutation of Lys 9 in SnoopTagJr, Asn 17 in DogTag, or Glu 61 in SnoopLigase abolished product formation (FIG. 2B).

Example 2

SnoopLigase-Mediated Peptide-Peptide Ligation

To validate the proposed mechanism of reaction and the specificity of residue ligation by SnoopLigase, SnoopTagJr and DogTag were fused to model proteins. DogTag was fused to Small Ubiquitin-like Modifier (SUMO), while SnoopTagJr was fused to an affibody against HER2. Mixing of SUMO-DogTag and SnoopTagJr-AffiHER2 with Snoop-Ligase led to the appearance of a new, higher molecular weight band, representing the covalently linked ligation product. The band had the expected molecular weight and was resistant to boiling in SDS loading buffer. Mutation of any of the three reactive triad residues (lysine at position 9 in SnoopTagJr, asparagine at position 17 in DogTag and glutamic acid at position 61 in SnoopLigase) prevented the occurrence of the ligation product band (FIG. 2B). Mass spectrometry gave the expected molecular weight change after reaction of peptide substrates.

Example 3

SnoopLigase Reaction Conditions

Figure 4:
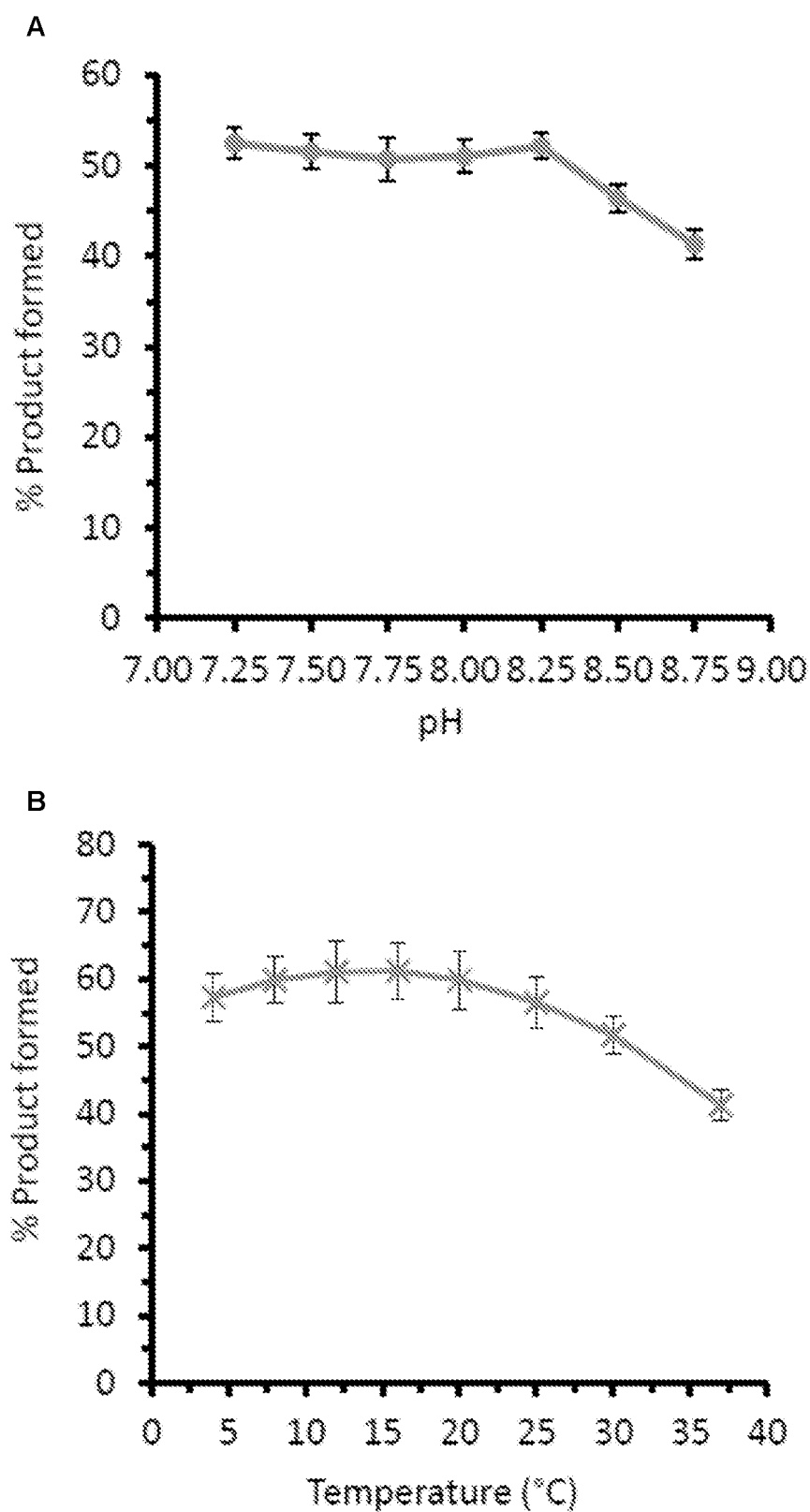
FIG. 4 shows graphs demonstrating the effect of (A) pH and (B) temperature on the activity of SnoopLigase ligating SnoopTagJr-AffiHER2 and SUMO-DogTag.
Figure 5:
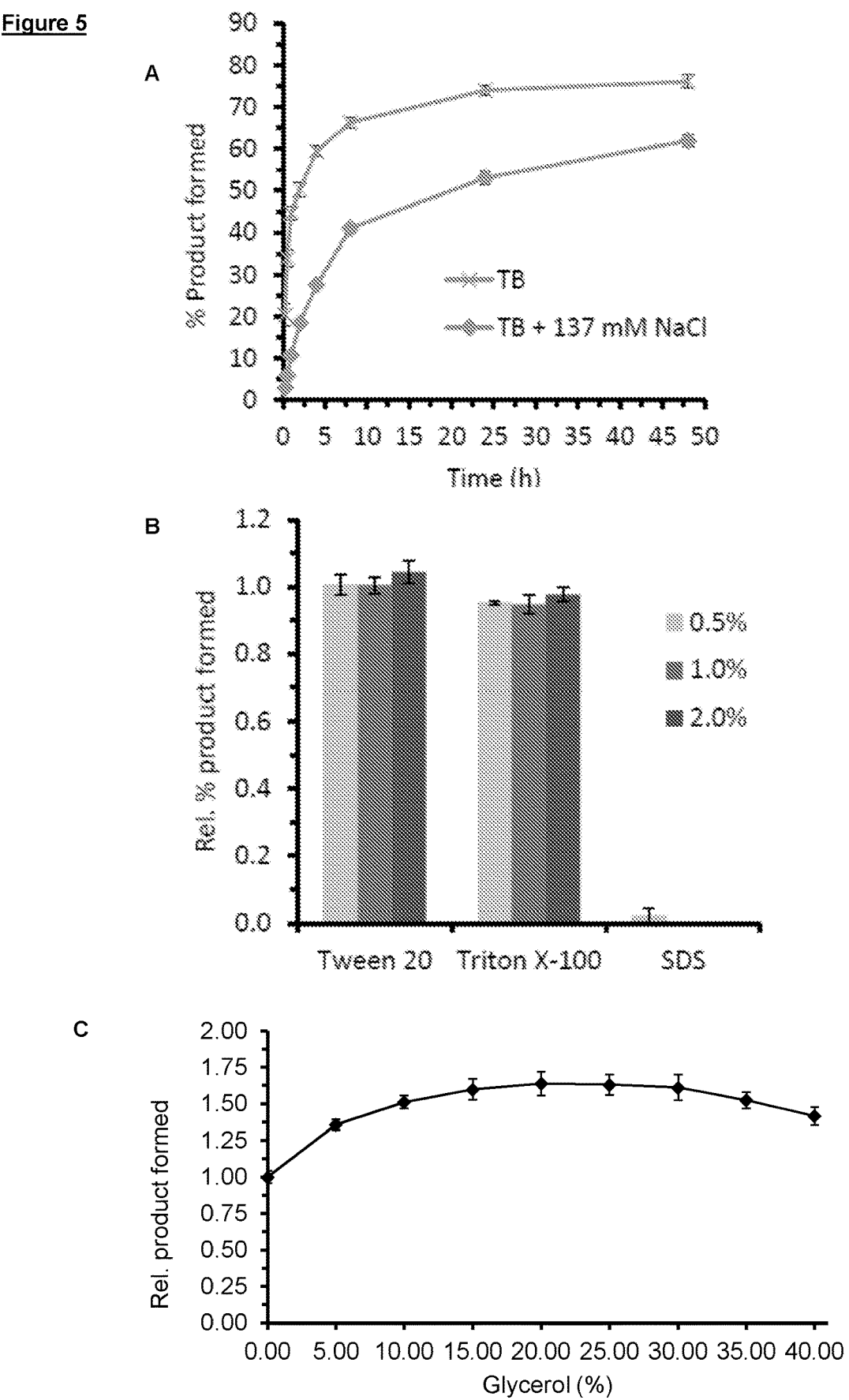
FIG. 5 shows graphs demonstrating the effect of (A) NaCl concentration, (B) detergents and (C) glycerol on the activity of SnoopLigase ligating SnoopTagJr-AffiHER2 and SUMO-DogTag.

SnoopLigase reaction functioned well around neutral pH, with little difference from 7.25 to 8.75 (FIG. 4A). Efficient ligation occurred over a wide range of temperatures (4-37° C.), with optimum at 15° C. (FIG. 4B). SnoopLigase was functional in the presence of extracellular concentrations of NaCl, although reaction proceeds most efficiently with Tris borate buffer in the absence of NaCl (FIG. 5A). SnoopLigase reacted well in the presence of the commonly used detergents Tween 20 and Triton X-100 up to 2%, but SDS inhibited the reaction (FIG. 5B). Addition of the protein stabilizer glycerol at 15-30% (v/v) enhanced reaction rate (FIG. 5C).

SnoopLigase had a melting temperature of 45° C. from DSC and regained full activity following heat treatments up to 70° C. Partial activity was restored following heating at 99° C.

Example 4

SnoopLigase Reaction Product Purification

Figure 3:
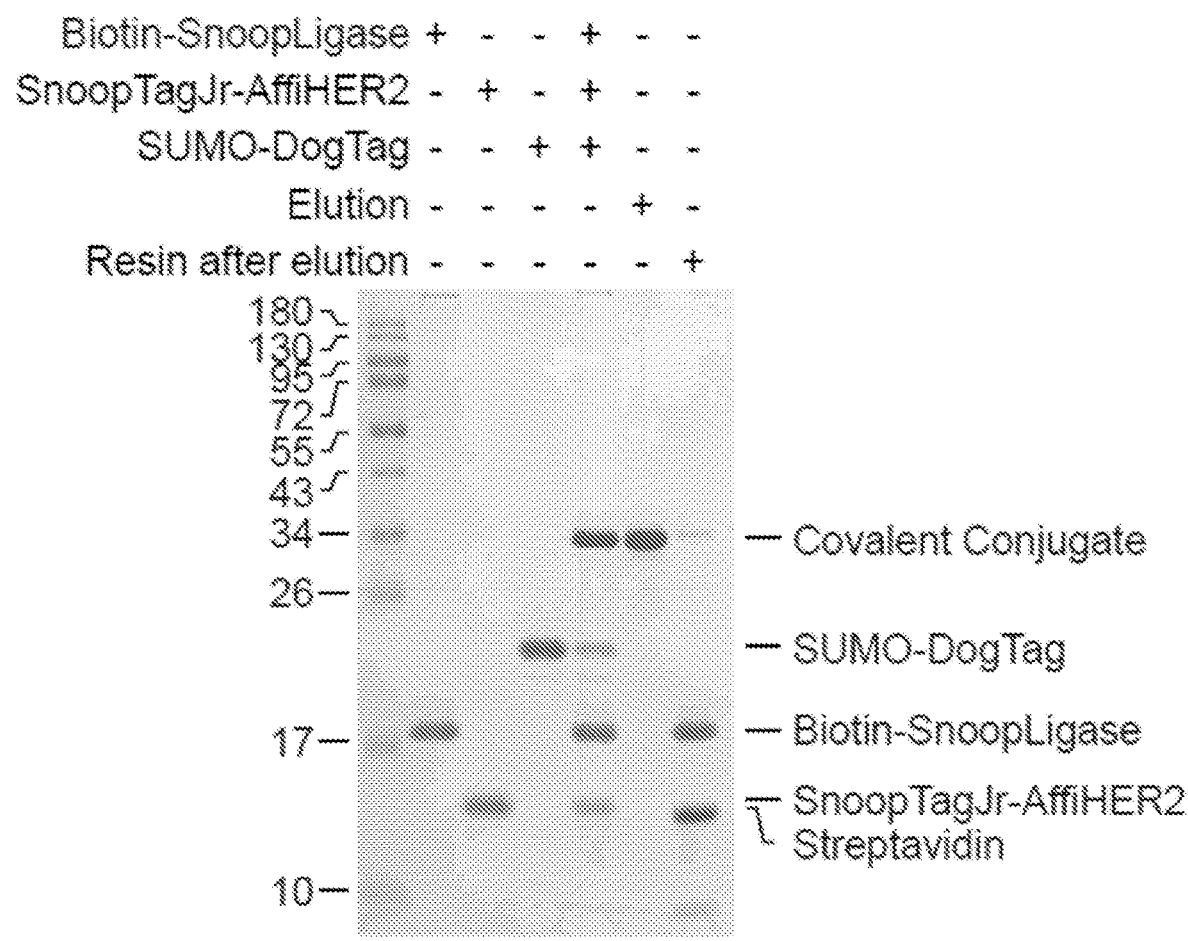
FIG. 3 shows a photograph of an SDS-PAGE gel with Coomassie staining characterising the analysis of products from the solid-phase ligation reaction described in Example 4.

Upon reaction, SnoopLigase bound strongly to the reaction product, which allowed efficient purification of ligation reaction product (FIG. 3A). After reacting SnoopTagJr-AffiHER2 with SUMO-DogTag using biotinylated Snoop-Ligase, the ligase was captured by streptavidin-agarose. The strong interaction between biotin-streptavidin and SnoopLigase-reaction product permits stringent washing, such that non-reacted proteins are removed. Incubation of the resin with antibody elution buffer did not affect the biotin-streptavidin interaction, but disrupted SnoopLigase-reaction product interaction and yielded high purity ligated product (FIG. 3A), removing non-reacted products and SnoopLigase. This procedure eliminates the need for subsequent time-consuming purification by size exclusion chromatography or dialysis. Furthermore, by tuning elution volume, highly concentrated ligation product could be eluted, irrespective of reactant concentrations used during reaction.

Example 5

SnoopLigase Solid Phase Reaction

Figure 6:
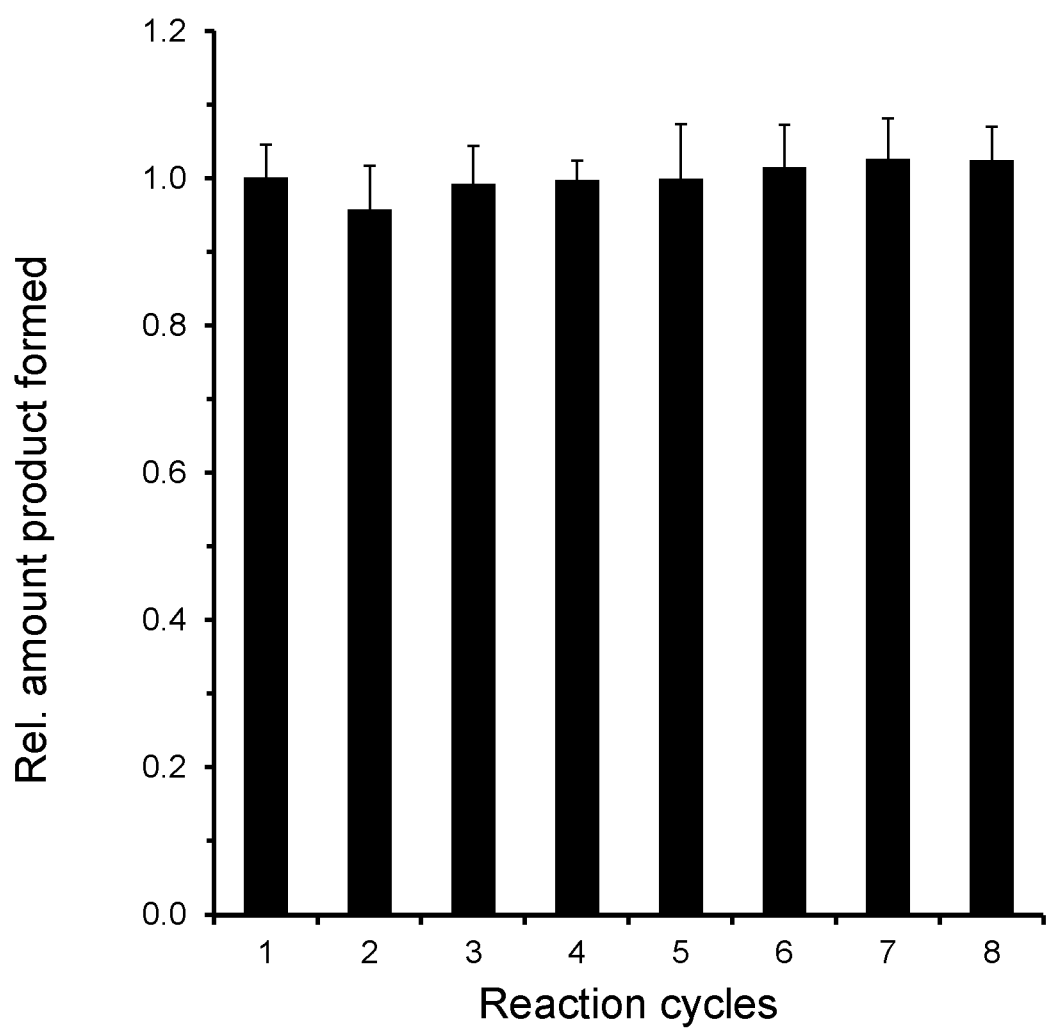
FIG. 6 shows a bar chart showing the relative amount of product formed in repeated reactions of SnoopLigase immobilised on a solid substrate following elution of the reaction product using low pH conditions. The product yield was normalised relative to the yield from reaction cycle 1. n=9, mean+/−1 S.D.

Immobilizing enzymes on a solid phase can improve reaction efficiency and can facilitate cost-effective re-use of purified enzymes. To test whether SnoopLigase can be "recycled" after antibody elution buffer treatment, the inventors immobilised biotinylated SnoopLigase on streptavidin agarose and performed a ligation reaction by addition of SnoopTagJr-AffiHER2 and SUMO-DogTag. Upon washing and elution of the reaction product, the SnoopLigase-coupled agarose resin was used for another ligation reaction. The amount of product formed remained constant for at least 8 reaction cycles, indicating that SnoopLigase can perform multiple turn-overs and treatment of SnoopLigase with low pH does not irreversibly denature the enzyme (FIG. 6).

Example 6

SnoopLigase Yield of Reaction

Figure 7:
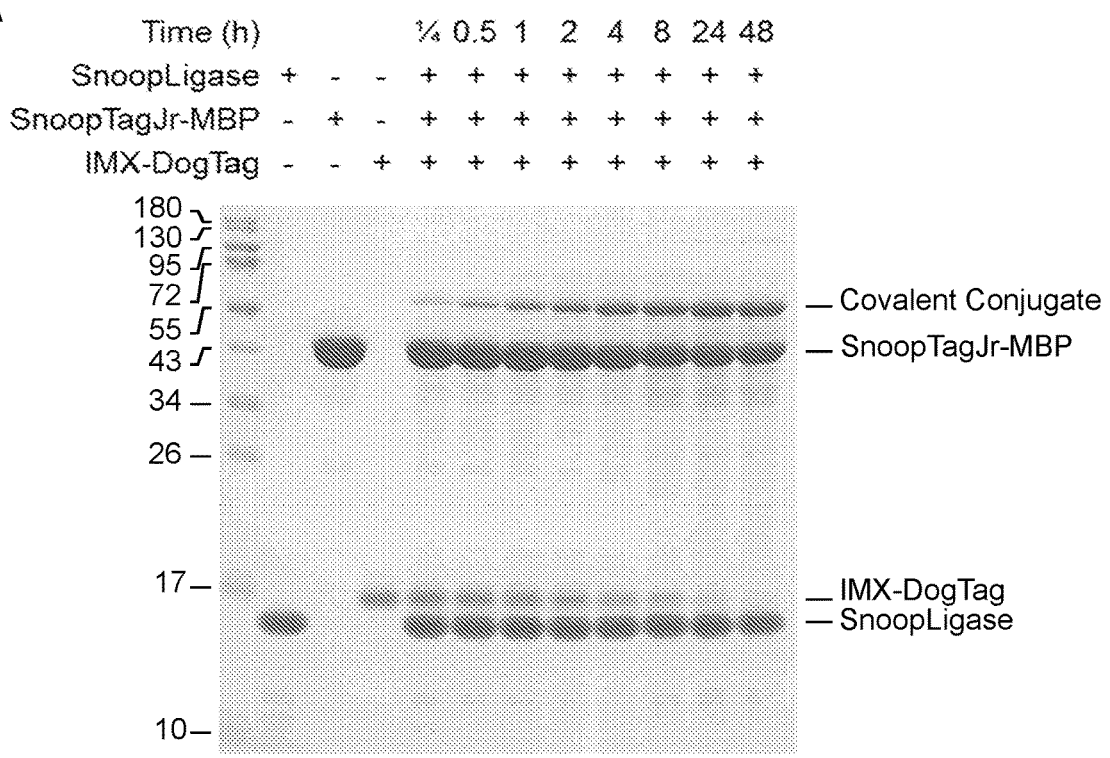
FIG. 7 shows (A) a photograph of an SDS-PAGE with Coomassie staining characterising the analysis of products from the reaction between IMX-DogTag and SnoopTagJr-MBP described in Example 6; and (B) a graph showing the quantification of the reaction described in (A) (n=3, mean+/−1 S.D).
Figure 7:
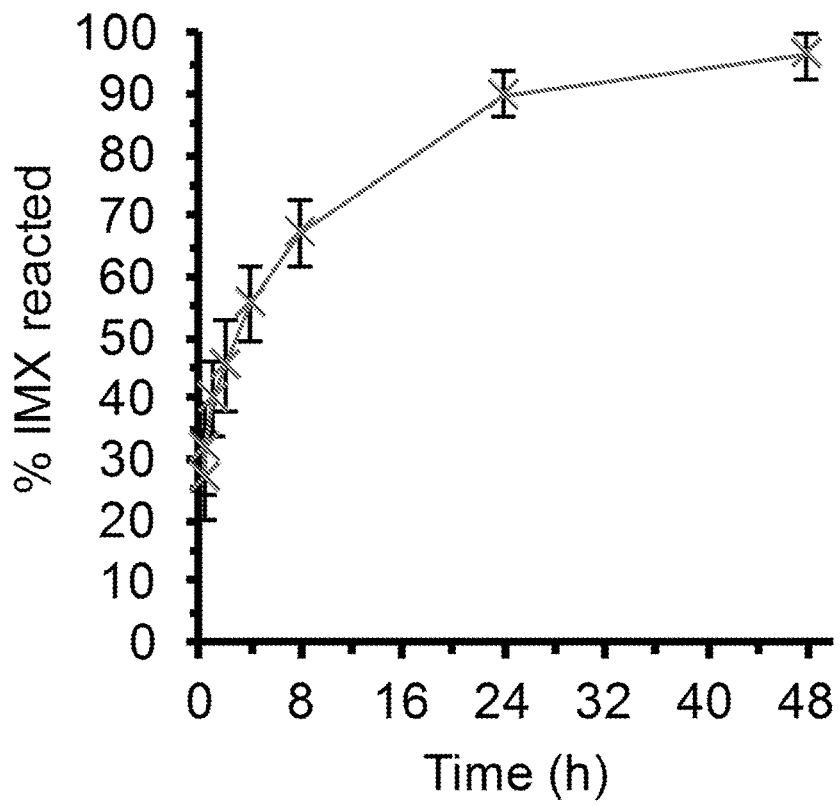

The yield of reaction between DogTag and SnoopTagJr catalysed by SnoopLigase was determined by incubating IMX-DogTag at 10 µM with 20 µM of each of SnoopLigase and SnoopTagJr-MBP in 50 mM TB pH 7.25+15% glycerol (v/v) for a variety of time periods, from 15 minutes to 48 hours, at 4° C. Samples were analysed using SDS-PAGE under reducing conditions with Coomassie staining and FIGS. 7A and B show that SnoopLigase facilitates the coupling of nearly all of the IMX-DogTag fusion protein. Notably, a reaction yield of 96% for IMX-DogTag was achieved after 48 h.

Figure 8:
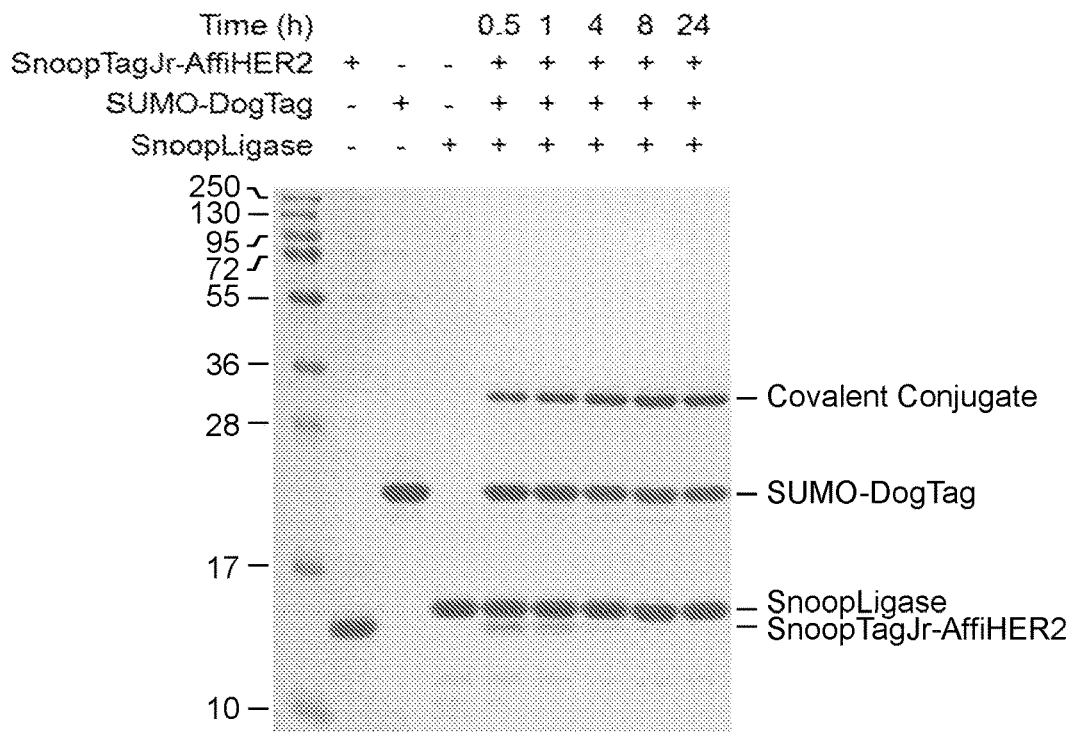
FIG. 8 shows (A) a photograph of an SDS-PAGE with Coomassie staining characterising the analysis of products from the reaction between SnoopTagJr-AffiHER2 and SUMO-DogTag described in Example 6; and (B) a graph showing the quantification of the reaction described in (A) (n=3, mean+/−1 S.D).
Figure 8:
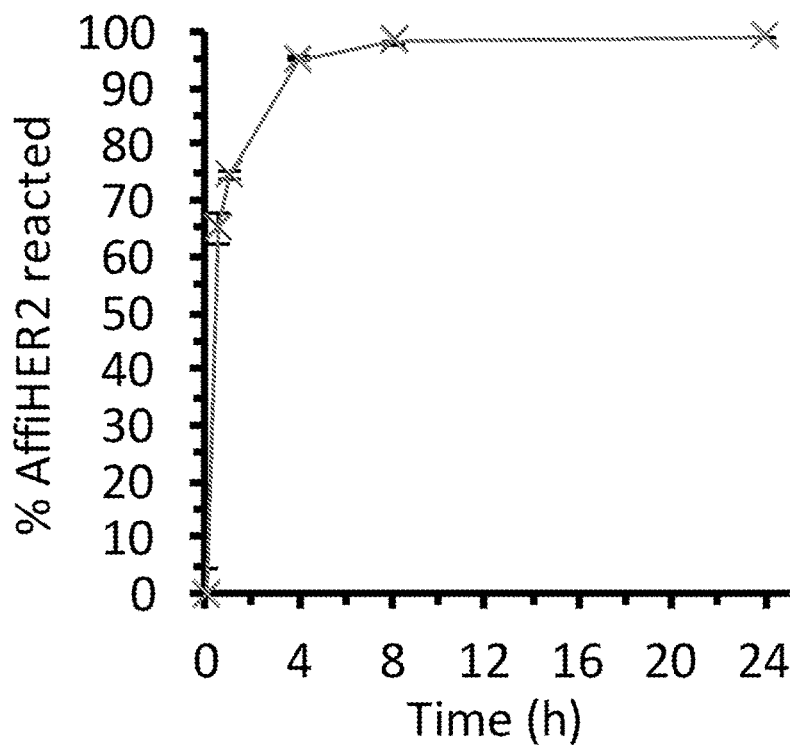

Similarly, FIGS. 8A and B show that incubating SnoopTagJr-AffiHER2 at 5 µM with 10 µM of each of SnoopLigase and SUMO-DogTag in 50 mM TB pH 7.25+15% glycerol (v/v) at 4° C. facilitates coupling of nearly all of the SnoopTagJr-AffiHER2 fusion protein after 24 hours, i.e. a reaction yield of 99% for SnoopTagJr-AffiHER2 was achieved after 24 hours.

Example 7

Alternative Conditions for Elution of the Reaction Product from a Solid Phase

Figure 9:
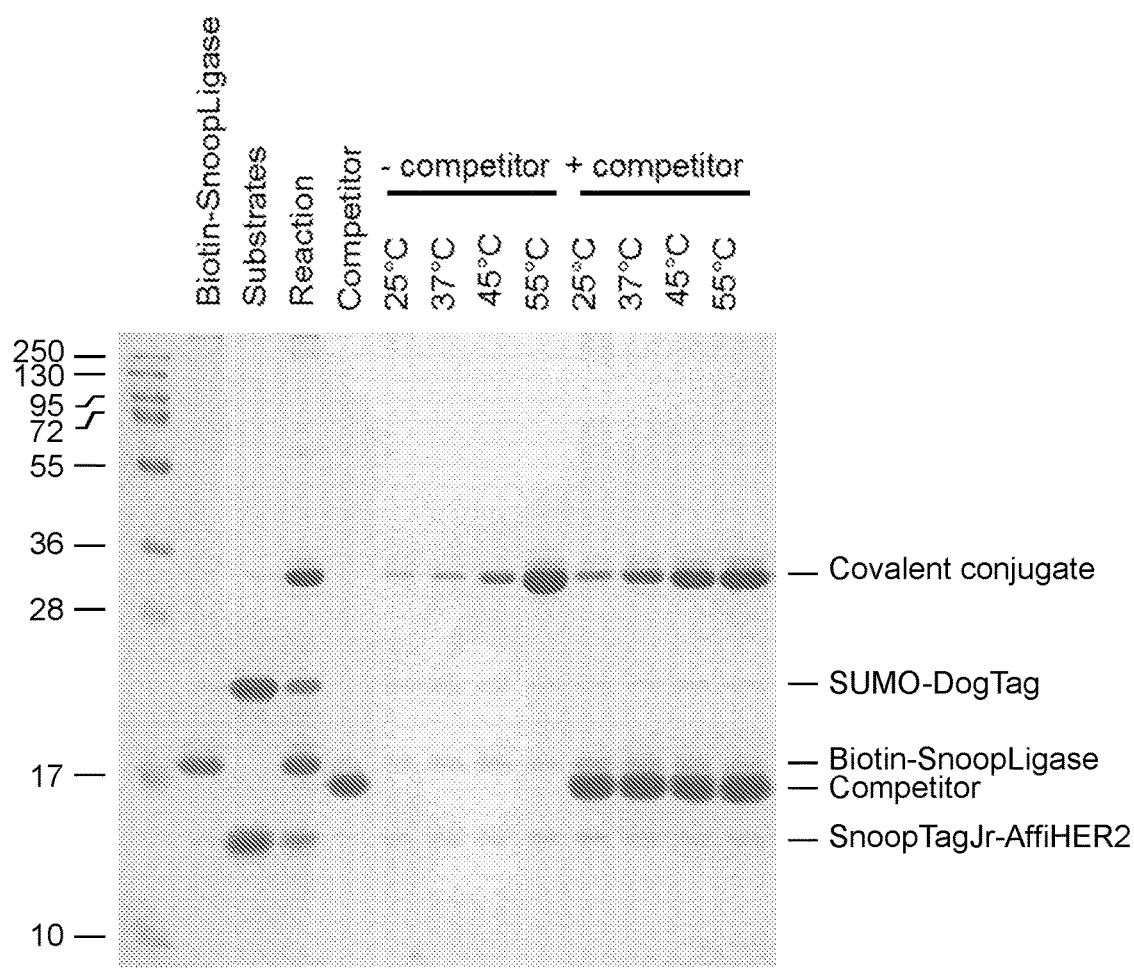
FIG. 9 shows a photograph of an SDS-PAGE with Coomassie staining characterising the analysis of temperature-dependent elution of product from SnoopLigase described in Example 7, wherein "Competitor" refers to SnoopTag peptide covalently linked to AffiHER2-DogTag.

The effect of temperature and competition on the elution of the reaction product from a solid phase was investigated using the SnoopTagJr-AffiHER2 and SUMO-DogTag fusion proteins and biotinylated SnoopLigase described in Example 5. The fusion proteins and SnoopLigase (50 µM each) were incubated in 50 mM TB pH 7.25+15% glycerol (v/v) for 5 h at 4° C. Biotin-SnoopLigase was pulled down using streptavidin agarose, and the resin was washed 5 times with 5 resin volumes of PBS. Elution was performed twice with 10 µl PBS with or without 35 µM of a competitor protein (SnoopTag peptide covalently linked to AffiHER2-DogTag), each for 5 min at temperatures ranging from 25-55° C. FIG. 9 shows that efficient elution was achieved at temperatures of 55° C. and the addition of a competitor protein enabled efficient elution at 45° C.

Example 8

Additive-Dependent Elution of Product from SnoopLigase

Twelve additives (shown in FIG. 10) were selected to determine whether they were capable of disrupting the non-covalent interaction between SnoopLigase and its reaction product.

Biotinylated SnoopLigase was incubated with SUMO-DogTag and SnoopTagJr-AffiHER2 at 50 µM each for 24 h at 4° C. Biotin-SnoopLigase was pulled down with streptavidin agarose and the resin was washed 5 times with 5 resin volumes of PT buffer (10 mM Tris phosphate, pH 6.5) at 25° C. Elution was performed twice with 4 resin volumes of PT buffer containing 16 µM AffiHER2-DogTag:SnoopTag protein competitor (described in Example 7) and one of the twelve selected additives indicated in FIG. 10, pH 6.5 for 5 min at 37° C. A control reaction used no additive in the elution buffer.

Figure 10:
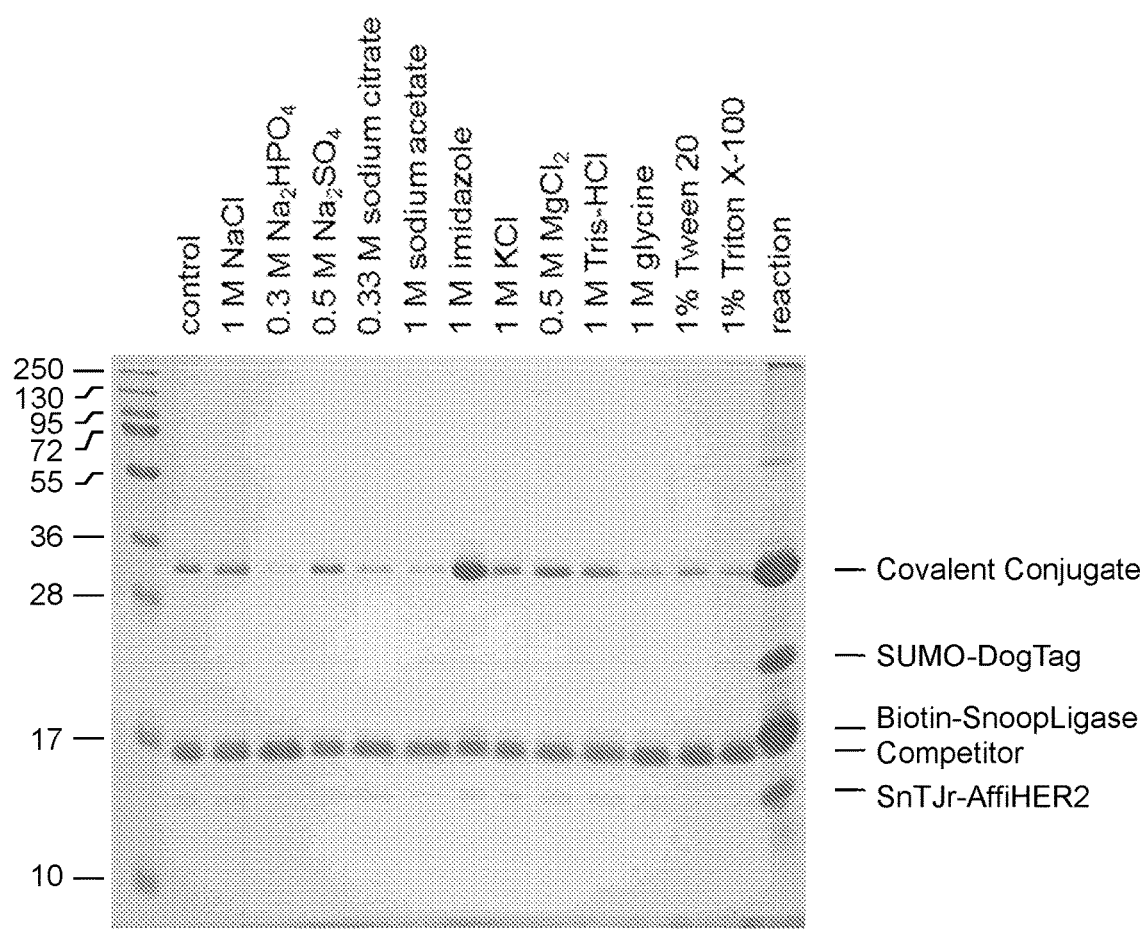
FIG. 10 shows a photograph of an SDS-PAGE with Coomassie staining characterising the analysis of additive-dependent elution of product from SnoopLigase described in Example 8, wherein "Control" is with no additive to the elution buffer and "Reaction" is the mixture before resin capture.

FIG. 10 shows that a solution comprising 1 M imidazole and the protein competitor resulted in efficient elution of the reaction product (covalent conjugate) from the solid phase.

The effect of different concentrations of imidazole in the absence of a protein competitor was investigated. SnoopTagJr-AffiHER2 and SUMO-DogTag were incubated with biotin-SnoopLigase at 50 µM each in 50 mM TB pH 7.25+15% glycerol (v/v) for 24 h at 4° C. Biotin-SnoopLigase was pulled down with streptavidin agarose resin and this resin was washed 4 times with 5 resin-volumes of PT buffer (25 mM Tris phosphate pH 7.0) at 25° C. Elution was performed with concentrations of imidazole ranging from 0.5-4 M, pH 7.0 in PT buffer at 25° C. for 5 min.

Figure 11:
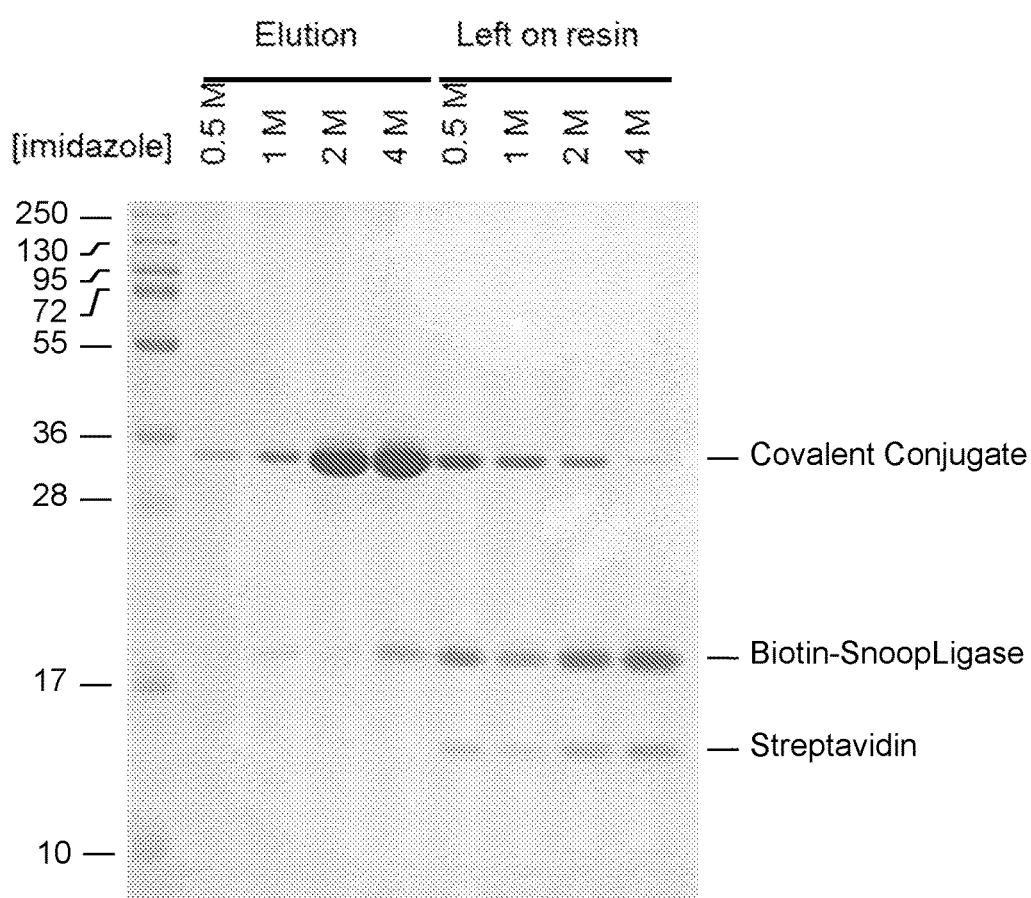
FIG. 11 shows a photograph of an SDS-PAGE with Coomassie staining characterising the analysis of imidazole titration for product elution from SnoopLigase described in Example 8. "Left on resin" refers to samples from boiling the resin after elution with SDS-loading buffer, to visualise what remained on the resin. This boiling released streptavidin subunits from the streptavidin-agarose.

FIG. 11 shows that a solution comprising 2 M imidazole is sufficient to efficiently elute the reaction product from the solid phase under physiologically relevant conditions, i.e. pH 7.0 and 25° C. Notably higher concentrations of imidazole resulted in elution of SnoopLigase and streptavidin from the solid phase.

Example 9

Comparison of SnoopTag (SEQ ID NO: 9) and SnoopTagJr (SEQ ID NO: 2) Activity

A comparative assay was performed to measure the difference in activity produced by modifying the SnoopTag (SEQ ID NO: 9) sequence to generate SnoopTagJr (SEQ ID NO: 2).

SnoopLigase and SUMO-DogTag at 10 µM each were incubated with 10 µM of either SnoopTag-AffiHER2 or SnoopTagJr-AffiHER2 in 50 mM TB pH 7.25+15% glycerol (v/v) for time intervals between 15 minutes to 24 hours at 4° C.

Figure 12:
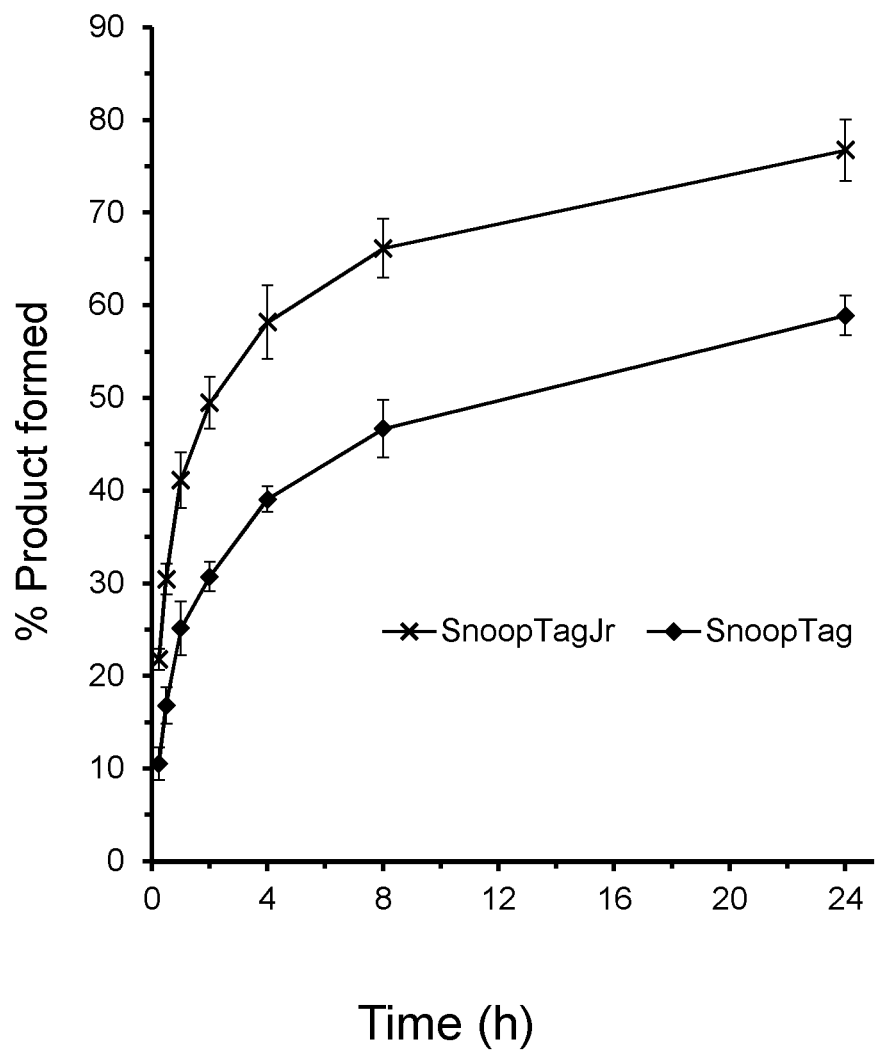
FIG. 12 shows a graph showing the amount of reaction product formed between SUMO-DogTag and either SnoopTag-AffiHER2 or SnoopTagJr-AffiHER2, catalysed by SnoopLigase (n=3, mean+/−1 S.D).

FIG. 12 shows that SnoopTagJr reacted more efficiently than SnoopTag at all time-points, as measured by the total amount of reaction product formed.

Example 10

Effect of Chemical Chaperone on SnoopLigase Activity

As described above, SpyLigase is capable of ligating its peptide tag substrates (SpyTag and KTag) only in the presence of a chemical chaperone TMAO (trimethylamine N-oxide). Accordingly, the activity of SnoopLigase in the presence of TMAO was assessed.

Figure 13:
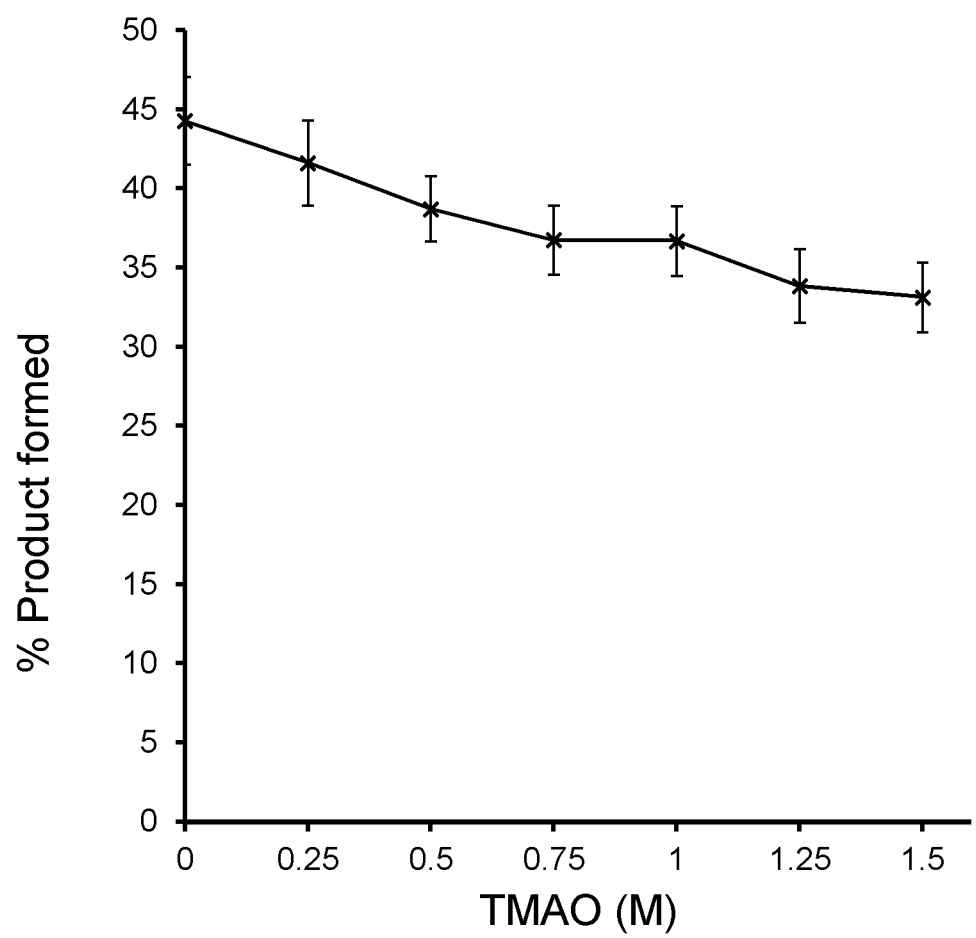
FIG. 13 shows a graph showing the amount of reaction product formed between SUMO-DogTag and SnoopTagJr-AffiHER2, catalysed by SnoopLigase at various concentrations of TMAO (n=3, mean+/−1 S.D).

SnoopLigase, SnoopTagJr-AffiHER2 and SUMO-DogTag at 10 µM each were incubated in 50 mM TB pH 7.25+15% glycerol+a range of concentrations of TMAO (from 0-1.5 M) for 1.5 h at 4° C. The activity of the SnoopLigase was assessed by measuring the amount of reaction product formed. FIG. 13 shows that the addition of TMAO to the reaction gave no improvement on SnoopLigase activity, which is able to function in the absence of TMAO.

Example 11

Assessment of DogTag (SEQ ID NO: 3) Reactivity at an Internal Site in a Fusion Protein To determine whether the peptide tags are capable of reacting with each other when at least one of the tags is located within a protein (i.e. where the tag forms an internal domain of a protein) DogTag (SEQ ID NO: 3) was inserted into the maltose binding protein (MBP) and HaloTag7. In particular, the DogTag sequence was flanked on either side by different lengths of linker sequences (2-8 amino acids) and inserted into MBP after residue 317 and before residue 319, deleting residue 318. The linker sequences flanking the peptide tag were repeats of Gly-Ser. The DogTag sequence flanked with 3 Gly-Ser repeats on either side was inserted into HaloTag7SS between residues D139 and E140. HaloTag7SS refers to HaloTag7 modified to replace cysteine residues at positions 61 and 261 with serine residues.

Figure 14:
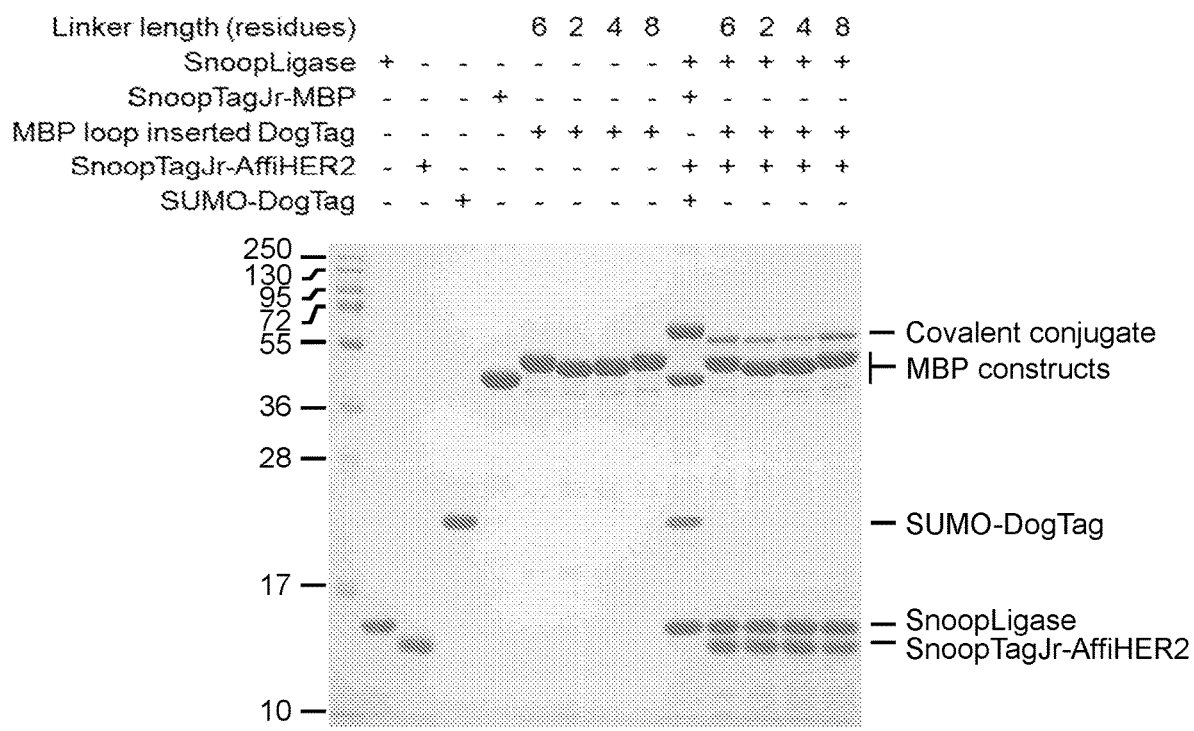
FIG. 14 shows a photograph of an SDS-PAGE with Coomassie staining characterising the analysis of the reactivity of DogTag-MBP internal fusion protein with SnoopTagJr-AffiHER2, catalysed by SnoopLigase described in Example 11.

The DogTag-MBP fusion proteins, SnoopTagJr-AffiHER2 and SnoopLigase at 10 µM each were incubated in 50 mM TB pH 7.25+15% glycerol for 4 h at 4° C. and analysed using SDS-PAGE with Coomassie staining. FIG. 14 shows that all four MBP-DogTag insertion constructs were reactive, with highest reactivity shown by linker lengths of 6 or 8 residues.

Figure 16:
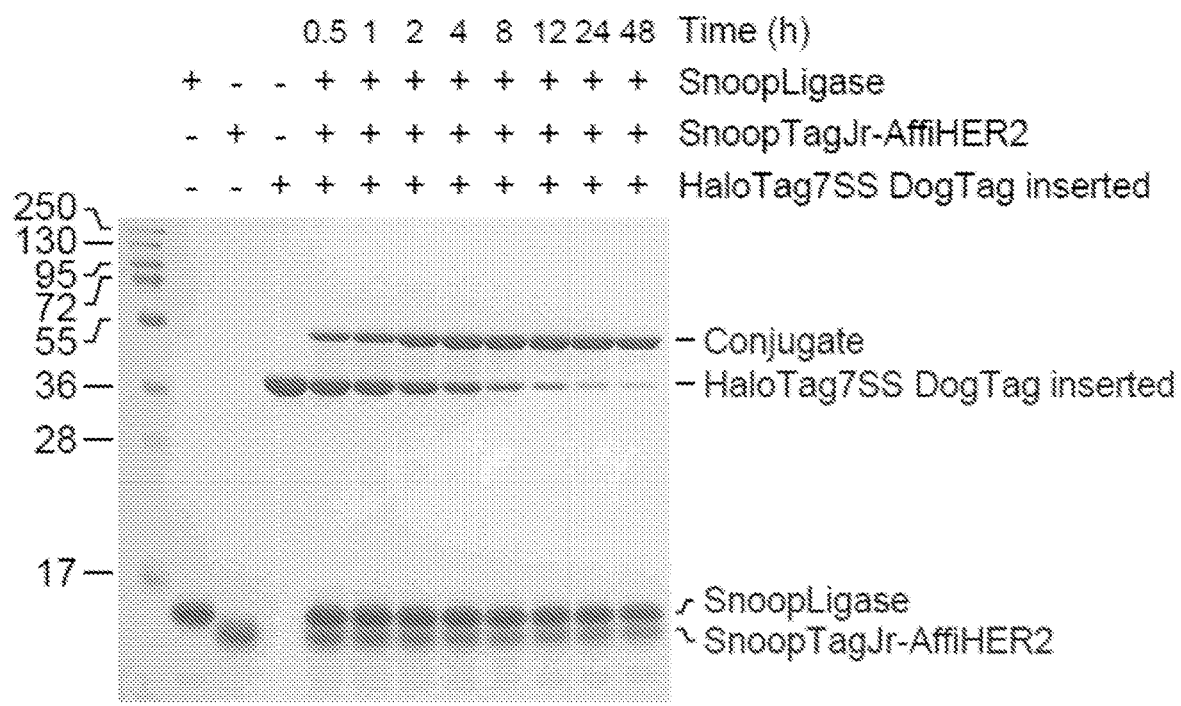
FIG. 16 shows a photograph of an SDS-PAGE with Coomassie staining characterising the analysis of products from the reaction between SnoopTagJr-AffiHER2 and HaloTag7SS-DogTag internal fusion protein, catalysed by SnoopLigase described in Example 11.

The DogTag-HaloTag7SS fusion protein (10 µM) was incubated with SnoopTagJr-AffiHER2 and SnoopLigase (both 20 µM) in 50 mM TB pH 7.25+15% glycerol for 0.5-48 h at 4° C. and analysed using SDS-PAGE with Coomassie staining. FIG. 16 shows that the DogTag- HaloTag7SS insertion construct was reactive, with a reaction yield of about 90% after 24 hours.

Example 12

Further Conditions for Elution of the Reaction Product from a Solid Phase

Figure 15:
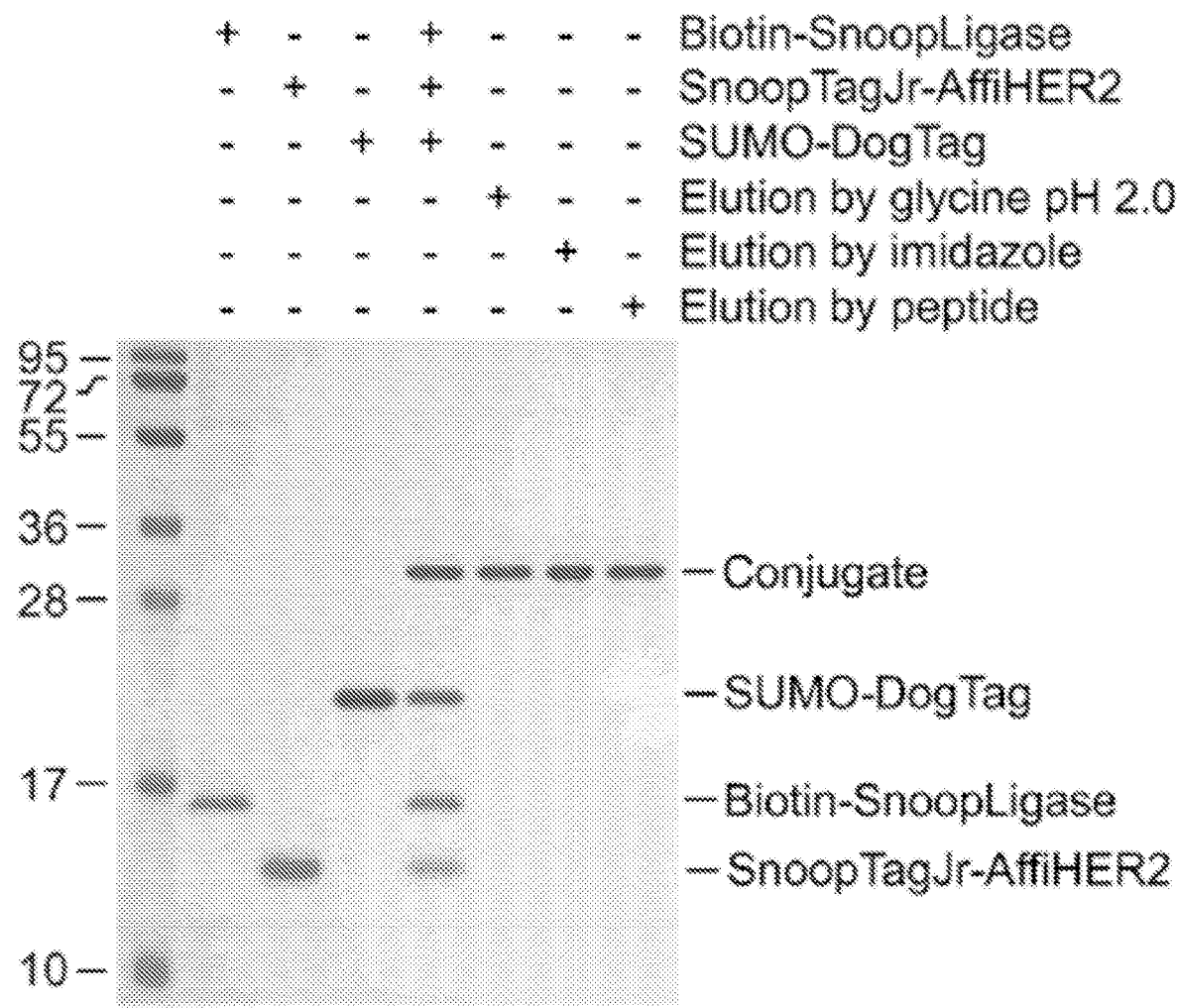
FIG. 15 shows a photograph of an SDS-PAGE with Coomassie staining characterising the analysis of different elution methods to separate the reaction product of SUMO-DogTag protein with SnoopTagJr-AffiHER2 from SnoopLigase. The "Elution by peptide" refers to elution using the SnoopTagJr:DogTag competitor peptide described in Example 12.

Examples 4, 7 and 8 demonstrate that the SnoopLigase reaction product may be eluted from a solid phase under a variety of conditions. However, incubation in pH 2.0 or 2M imidazole or at relatively high temperatures may not be suitable for all proteins. The inventors confirmed that a SnoopTagJr:DogTag peptide conjugate is capable of outcompeting the SnoopLigase reaction product with equivalent efficiency to an antibody elution buffer (glycine pH 2.0) and 2M imidazole (FIG. 15).

The SnoopTagJr:DogTag competitor peptide was generated via SUMO-DogTag and SUMO protease. SUMO-DogTag and SnoopTagJr peptide were covalently conjugated using SnoopLigase immobilized on a solid phase via HaloTag7. The reaction product (SUMO-DogTag:SnoopTagJr) was eluted using imidazole as described above. The reaction product was then incubated with SUMO-protease Ulp1, which cleaves the DogTag:SnoopTagJr peptide from SUMO. Incubation of the reaction product with Ni-NTA depleted the His-tagged SUMO and Ulp1 proteins yielding a purified DogTag:SnoopTagJr peptide.

The competitor peptide allowed clean elution of the SnoopLigase reaction product (SUMO-DogTag:SnoopTagJrAffiHER2) from biotin-SnoopLigase immobilized on an streptavidin-agarose column (FIG. 15) under physiological conditions, i.e. 37° C. Solid-phase purification eliminated the need for subsequent separation of the reaction product from SnoopLigase and unreacted starting materials by size exclusion chromatography, which is time-consuming and often leads to substantial losses.

Example 13

Assessment of DogTag (SEQ ID NO: 3) and SnoopTagJr (SEQ ID NO: 2) Reactivity as N- or C-Terminal Fusions in a Variety of Proteins To validate that the peptide tags may be used as universal linkers, the tags were fused to various proteins (AffiHER2, SUMO, mClover3, MBP, mEGFP, and HaloTag7SS) at the N- or C-terminus and tested in combinations. The DogTag-linked protein (10 μM [Table 2] or 20 μM [Table 3]) was incubated with the SnoopTagJr-linked protein (20 μM [Table 2] or 10 μM [Table 3]) and SnoopLigase (20 μM) in 50 mM TB pH 7.25+15% glycerol for 24 h at 4° C. and analysed using SDS-PAGE with Coomassie staining. Tables 2 and 3 show the percentage of DogTag partner and SnoopTagJr partner reacted, respectively. N/A refers to reactions in which band overlap prevented quantification. The order of the components listed below indicated whether the tag was N-terminal or C-terminal, i.e. AffiHER2-DogTag refers to DogTag linked to the C-terminus of AffiHER2, DogTag-mClover3 refers to DogTag linked to the N-terminus of mClover3.

The results show that most of the combinations had a reaction yield of more than 95%, thereby demonstrating that the peptide tags react efficiently when located at the N- and C-terminus of diverse proteins.

TABLE 2

Percentage of DogTag partner reacted
10 μM DogTag partner

| | | AffiHER2-DogTag | SUMO-DogTag | DogTag-mClover3 | MBP-DogTag |
|---|---|---|---|---|---|
| 20 μM SnoopTagJr partner | SnoopTagJr-AffiHER2 | 99.9 ± 0.02 | 99.9 ± 0.01 | 94.0 ± 0.3 | 98.4 ± 00.2 |
| | SnoopTagJr-mEGFP | 99.9 ± 0.04 | 99.1 ± 1.3 | 82.3 ± 2.1 | 87.8 ± 0.1 |
| | HaloTag7SS-SnoopTagJr | 99.95 ± 0.03 | 99.7 ± 0.5 | 96.1 ± 0.5 | 97.0 ± 1.0 |
| | MBP-SnoopTagJr | 99.95 ± 0.03 | 99.0 ± 0.9 | 85.4 ± 0.7 | 95.0 ± 4.8 |

TABLE 3

Percentage of SnoopTagJr partner reacted
20 μM DogTag partner

| | | AffiHER2-DogTag | SUMO-DogTag | DogTag-mClover3 | MBP-DogTag |
|---|---|---|---|---|---|
| 10 μM SnoopTagJr partner | SnoopTagJr-AffiHER2 | 99.95 ± 0.04 | 99.9 ± 0.1 | 99.8 ± 0.2 | 99.95 ± 0.05 |
| | SnoopTagJr-mEGFP | 99.9 ± 0.05 | 99.95 ± 0.03 | 89.4 ± 3.4 | 99.7 ± 0.3 |
| | HaloTag7SS-SnoopTagJr | 99.3 ± 0.03 | 99.0 ± 0.1 | 98.0 ± 0.2 | N/A |
| | MBP-SnoopTagJr | 93.3 ± 0.3 | 99.1 ± 0.2 | 79.5 ± 1.6 | N/A |

Example 14

SnoopLigase Reactivity is Tolerant to Lyophilisation and Reducing Agents

Figure 17:
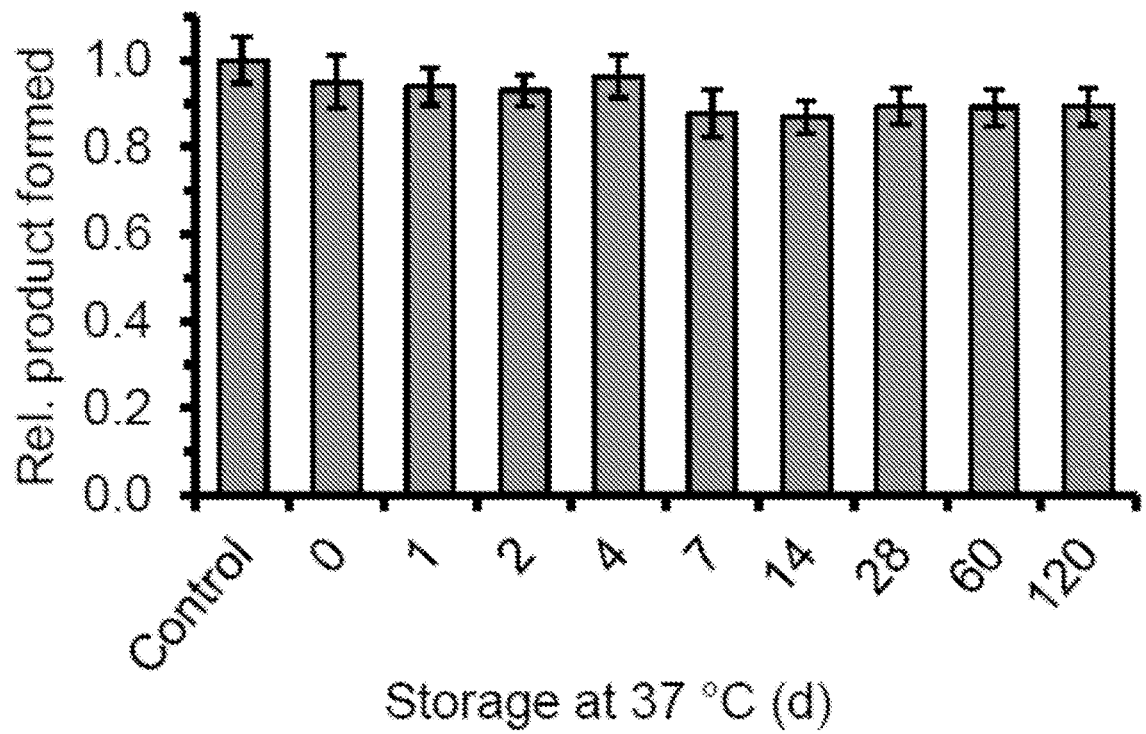
FIG. 17 shows (A) a bar chart showing the activity of lyophilized SnoopLigase following storage at 37° C. for the specified numbers of days relative to the activity of a non-lyophilized sample as described in Example 14, and (B) a bar chart showing the activity of SnoopLigase with reducing agents relative to SnoopLigase without reducing agents as described in Example 14.
Figure 17:
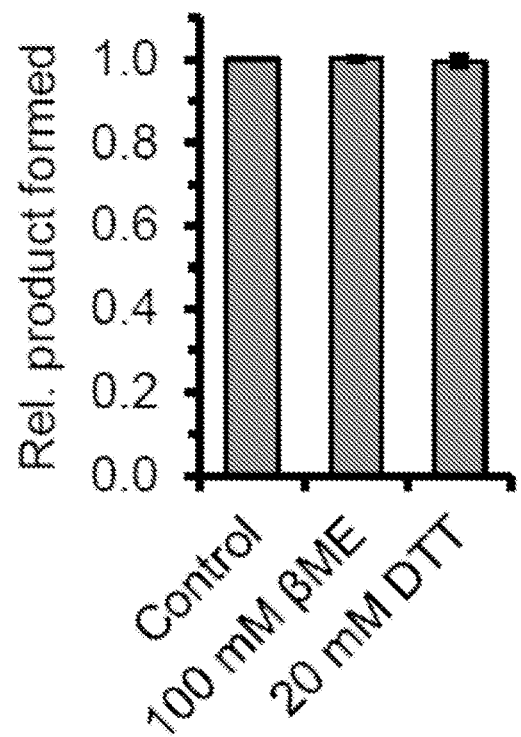

SnoopLigase was lyophilized and stored for 0-120 days at 37° C. At various timepoints, samples of lyophilized SnoopLigase were reconstituted in reaction buffer with SnoopTagJr-AffiHER2 and SUMO-DogTag (10 μM each) for 2 hours at 4° C. in TB pH 7.25 with 15% (v/v) glycerol. FIG. 17A shows the product formation relative to the non-lyophilized control sample and demonstrates that nearly all of the activity was retained following reconstitution.

Since there are no cysteines in SnoopLigase or the peptide tags it was hypothesized that the reaction would be unaffected by reducing agents. This was confirmed by performing the reaction described above with or with reducing agent: 100 mM β-mercaptoethanol (βME) or 20 mM dithiothreitol (DTT). FIG. 17B shows the product formation relative to a control reaction without reducing agent and demonstrates that reducing agents do not affect SnoopLigase activity.

Methods

Cloning

Plasmid constructs for protein expression were cloned using standard PCR procedures and Gibson isothermal assembly. Nucleotide sequences of gene inserts were validated by Sanger sequencing. Constructs for expression in *E. coli* contained an N-terminal His$_6$-tag followed by a flexible GS-rich linker.

The sequence of RrgA is from Protein Data Bank ID code 2WW8.

Protein Expression and Purification

Expression plasmids were transformed into *E. coli* BL21 (DE3)-RIPL (Agilent) and cells were grown on LB-Agar plates containing 50 μg/ml kanamycin for 16 h at 37° C. Individual colonies were grown in 2×YT with 0.8% (w/v) glucose, 50 μg/ml kanamycin for 16 h at 37° C., 200 rpm. Starter cultures were diluted 1:100 in 1 L 2×YT with 0.8% (w/v) glucose, 50 μg/mL kanamycin and grown at 37° C., 200 rpm until A$_{600}$ of 0.5 was reached. Cultures were induced with 0.42 mM IPTG and grown for 4 h at 30° C., 200 rpm before harvesting. Proteins were purified using standard Ni-NTA methods (Qiagen) and dialysed three times 1:1000. Buffers for dialysis were TB (50 mM Tris•HCl pH-adjusted with boric acid) pH 8.0 for AP-SnoopLigase (where AP is a substrate peptide for BirA biotinylation) and SnoopTagJr-MBP, 50 mM boric acid pH 10.0 for RrgALigase (and point mutants), SnoopLigase, SnoopTag-AffiHER2, SnoopTagJr-AffiHER2 and SUMO-DogTag.

SnoopLigase In Vitro Reconstitution

To assess the formation of the isopeptide bond between SnoopTagJr and DogTag mediated by SnoopLigase, proteins were incubated at 10 μM each in TB pH 7.25+15% (v/v) glycerol at 4° C. for 2 h, unless indicated otherwise. To terminate the reaction, 6×SDS loading buffer (0.23 M Tris•HCl, pH 6.8, 24% (v/v) glycerol, 120 μM bromophenol blue, 0.23 M SDS) was added to a final concentration of 1×. Samples were heated for 3 min at 95° C. and allowed to cool to 25° C. for 10 min before loading.

Identification of SnoopLigase Point Mutations

To identify residues for proline substitution, Ramachandran analysis of amino acid residues in RrgA (PDB code 2WW8) was performed using MolProbity. Residues with φ-angles of −70° to −50° and location in loop regions were considered for proline substitution. To use the PROSS server, a separate multiple sequence alignment (MSA) was generated. Homologous sequences for RrgA residues 734-860 were collected using Position-Specific Iterative Basic Local Alignment Search Tool (PSI-BLAST). A MSA was generated using Multiple Sequence Comparison by Log-Expectation (MUSCLE). Cluster Database at High Identity with Tolerance (CD-HIT) was used to minimise sequence redundancy and tune the size of the dataset. The modified MSA and residues 734-860 of the RrgA PDB structure 2WW8 were fed into the PROSS server. The suggested amino acid substitutions were reviewed manually.

SnoopLigase Biotinylation

Biotinylation of AP-SnoopLigase was performed by incubating 220 μM AP-SnoopLigase with 14.7 μM GST-BirA, 0.5 mM MgCl$_2$, 3.3 mM D-biotin and 1 mM ATP in TB pH 8.0 for 1 h at 25° C. The same amount of GST-BirA and D-biotin was added again and the mixture was incubated for 1 h at 25° C. To deplete GST-BirA, the sample was incubated with 0.1 mL of glutathione-HiCap resin for 30 min at 25° C. on a sample rotor and centrifuged for 30 s at 17,000 g. The supernatant was collected and dialysed three times 1:1000 into TB pH 8.0.

Purification of SnoopLigase Reaction Product

SUMO-DogTag, SnoopTagJr-AffiHER2 and biotinylated SnoopLigase at 10 μM each in TB pH 7.25 with 15% (v/v) glycerol in a total volume of 200 μL were incubated for 20 h at 4° C. To capture SnoopLigase, 25 μL washed and equilibrated HiCap Streptavidin Agarose (Thermo Fisher, 20357) was added and samples were incubated for 30 min at 25° C. on a tube rotor. The resin was collected in a 1 mL poly-prep column (Bio-Rad) and spun for 1 min at 300 g. After washing the resin twice with 125 μL 50 mM glycine pH 3.0 with 300 mM NaCl and three times with 125 μL 50 mM glycine pH 3.0, one extra spin for 1 min at 500 g ensured the removal of excess liquid from the resin. To elute the SnoopLigase reaction product, the resin was incubated with 25 μL antibody elution buffer (50 mM glycine pH 2.0) for 1 min, before spinning the eluate into a tube containing 2.5 μL 1 M Tris•HCl for 1 min at 300 g. The elution was repeated twice more.

Mass Ppectrometry

SUMO-DogTag at 75 μM and SnoopTag solid-phase synthesized peptide (GKLGDIEFIKVNKGY, SEQ ID NO: 11 Insight Biotechnology at 95% purity) at 300 μM were incubated with 75 μM biotinylated SnoopLigase in TB pH 7.25 and 15% (v/v) glycerol in a total volume of 200 μL for 36 h at 4° C. The reaction product was purified as above, but with 100 μL HiCap Streptavidin Agarose and 500 μL wash buffers. Analysis was performed using a Micromass LCT time-of-flight electrospray ionisation mass spectrometer (Micromass). The molecular mass profile was created from the m/z spectrum using the V4.00.00 software (Waters) with a maximum entropy algorithm. Molecular masses of proteins were predicted by ExPASy ProtParam, based on amino acid sequence without N-terminal fMet and loss of ammonia (17.0 Da) during isopeptide bond formation.

Solid-Phase Ligation Reaction Cycles

Biotinylated SnoopLigase at 50 μM in TB pH 8.0 was coupled to 10 μL washed and equilibrated HiCap Streptavidin Agarose (Thermo Fisher) in a total volume of 50 μL for 30 min at 25° C. on a tube rotor. The resin was collected in a 1 mL poly-prep column (Bio-Rad) and spun for 1 min at 300 g, followed by five washes with 100 μL TB pH 8.0. The reaction was started by addition of 50 μL reaction mix (100 μM SUMO-DogTag and 100 μM SnoopTagJr-AffiHER2 in TB pH 7.25 with 15% (v/v) glycerol) and the sample was incubated for 3 h at 25° C. on a thermomixer at 800 rpm. The reaction mixture was spun for 1 min at 300 g and the resin washed twice with 50 μL 50 mM glycine pH 3.0 with 300 mM NaCl and three times with 50 μL 50 mM glycine pH 3.0. One extra spin for 1 min at 500 g ensured the removal of excess liquid from the resin. To elute the SnoopLigase reaction product, the resin was incubated with 10 μL antibody elution buffer for 1 min, before spinning the eluate into a tube containing 1 μL 1 M Tris•HCl for 1 min at 300 g. The elution was repeated three more times. The resin was washed twice with 100 μL 50 mM glycine pH 2.0 and twice with 100 μL TB pH 7.25. The reaction cycle was repeated three more times.

SnoopLigase Thermostability Test

SnoopLigase at 12.5 μM in TB pH 7.25 with 15% (v/v) glycerol was incubated at the indicated temperature for 15 min and cooled to 4° C. for 5 min. Heat-treated SnoopLigase was used for ligation of SnoopTagJr-AffiHER2 and SUMO-DogTag.

SDS-PAGE and Reaction Quantification

Gels were stained with InstantBlue Coomassie stain (Expedeon), destained with MilliQ water and imaged using a ChemiDoc XRS imager with ImageLab software (Bio-Rad). ImageLab was also used for band quantification. The percentage of tags reacted was calculated from band intensities as [product band]/([product band]+[leftover substrate bands]). Relative reactivity was calculated as percent tags reacted of ([sample]/[control]).

Production of DogTag:SnoopTagJr Competitor

A 4 mL amount of HaloTag7-SnoopLigase at 20 μM in 50 mMTB pH7.25 with 0.01% (v/v) Tween20 was incubated with 500 μL of packed HaloLink resin (Promega) for 2 h at 25° C. on a tube rotor. The sample was split into five buffer-equilibrated 1 mL polyprep columns (Bio-Rad) and spun for 1 min at 300 g at 25° C. Each resin sample was washed twice with 500 μL of 50 mM TB pH 7.25 with 0.01%(v/v) Tween 20. Columns were capped, and 200 μL of reaction buffer [50 μM SUMO-DogTag and 75 μM SnoopTagJr peptide in TB pH7.25 with 15% (v/v) glycerol] was added to each column. SnoopTagJr peptide was solid-phase synthesized by Activotec at >95% purity. After incubation for 4 h at 25° C. at 300 rpm on a Thermomixer, samples were spun for 1 min at 300 g at 25° C., and each resin sample was washed five times with 640 μL of Tris-phosphate pH7.0 with 0.5M imidazole and 0.01%(v/v) Tween 20. To elute the SnoopLigase reaction product, each resin sample was incubated with 100 μL of Tris-phosphate with 2.5M imidazole pH7.0 and 0.01% (v/v) Tween20 for 2 min at 25° C. on a Thermomixer at 800 rpm, before spinning the eluate into a tube for 1 min at 300 g, at 25° C. The elution was repeated twice more, and each resin washed twice with 500 μL of TB pH 7.25 with 0.01% (v/v) Tween 20. To start the next reaction cycle, fresh reaction mix was added to the resin and the reaction and purification procedure repeated. Six reaction cycles were performed in total. All elutions were pooled and dialyzed into TB pH7.5, and SUMO-DogTag:SnoopTagJr was concentrated to 118 μM using a 10 kDa MWCO spin filter (Sartorius). SUMO protease Ulp1 was added at 1:50 molar ratio to a final concentration of 2.4 μM, followed by a 45 min incubation at 25° C. After reaction, Tween20 was added to a final concentration of 0.01% (v/v). To deplete His-tagged proteins (SUMO and Ulp1), 600 μL of sample was incubated with 150 μL of packed Ni-NTA agarose (Qiagen) for 1 h at 25° C. on a tube rotor, the sample was centrifuged for 1 min at 16900 g at 25° C., and the supernatant containing the DogTag:SnoopTagJr conjugate was collected. The concentration was calculated using the OD280 extinction coefficient from ExPASy ProtParam.

SnoopLigase Removal by Peptide Elution

SUMO-DogTag, SnoopTagJr-AffiHER2, and biotin-SnoopLigase at 10 μM each in TB pH 7.25 with 15% (v/v) glycerol in a total volume of 150 μL were incubated for 16 h at 4° C. Tween20 was added to a final concentration of 0.01% (v/v). To capture biotin-SnoopLigase, 15 μL of washed and equilibrated HiCapstreptavidin-agarose (Thermo Fisher) was added, and the sample incubated for 30 min at 25° C. on a tube rotor. The resin was collected in a PCR tube (StarLab) and spun for 1 min at 300 g at 25° C., followed by five washes with 75 μL of Tris-phosphate pH7.0 with 0.01% (v/v) Tween20. A 30 μL amount of DogTag:SnoopTagJr in TB pH7.5 with 0.01% (v/v) Tween20 was added, and the sample incubated for 4 h at 37° C. at 800 rpm on a Thermomixer. The sample was centrifuged for 1 min at 16900 g and the supernatant collected.

Lyophilization Stability

Aliquots of 30 μL of SnoopLigase at 10 μM in TB pH 7.25 were prepared in 100 μL thin-wall PCR tubes (StarLab). Samples were flash-frozen in a dry ice-ethanol bath for 10 min and lyophilized using a BenchTop 2K freeze-dryer (VirTis) for 48 h at 0.14 mbar and −72.5° C. Lyophilized samples were stored at 37° C. for the indicated time in a glass scintillation vial sealed with Parafilm (Sigma-Aldrich) on a bed of Drierite (Sigma-Aldrich) to minimize sample hydration. Samples were reconstituted in reaction buffer and there action of SnoopTagJr-AffiHER2 and SUMO-DogTag was performed for 2 h at 4° C., followed by SDS-PAGE, Coomassie staining, and densitometry.

The invention claimed is:

1. A polypeptide comprising:
   a) an amino acid sequence as set forth in SEQ ID NO: 1; or
   b) an amino acid sequence with at least 80% sequence identity to a sequence as set forth in SEQ ID NO: 1, wherein said amino acid sequence comprises a glutamic acid at position 61 and one or more of the following:
      1) proline at position 66;
      2) proline at position 95;
      3) glycine at position 96; and
      4) valine at position 97,
   wherein the specified amino acid residues are at positions equivalent to the positions in SEQ ID NO: 1 and wherein said polypeptide is capable of promoting the formation of an isopeptide bond between the lysine residue at position 9 of SEQ ID NO: 2 and the asparagine residue at position 17 of SEQ ID NO: 3.

2. The polypeptide of claim 1, wherein said polypeptide comprises an amino acid sequence with at least 80% sequence identity to a sequence as set forth in SEQ ID NO: 1 and wherein said amino acid sequence comprises a glutamic acid at position 61 and two or more of the following:
   1) proline at position 66;
   2) proline at position 95;
   3) glycine at position 96; and
   4) valine at position 97.

3. The polypeptide of claim 1, wherein said polypeptide comprises an amino acid sequence with at least 80% sequence identity to a sequence as set forth in SEQ ID NO: 1 and wherein said amino acid sequence comprises a glutamic acid at position 61 and three or more of the following:
   1) proline at position 66;
   2) proline at position 95;
   3) glycine at position 96; and
   4) valine at position 97.

4. The polypeptide of claim 1, wherein said polypeptide comprises an amino acid sequence with at least 80% sequence identity to a sequence as set forth in SEQ ID NO: 1, wherein said amino acid sequence comprises a glutamic acid at position 61 and all of the following:
   1) proline at position 66;
   2) proline at position 95;
   3) glycine at position 96; and
   4) valine at position 97.

5. The polypeptide of claim 1, wherein the polypeptide comprises a threonine at position 100.

6. The polypeptide of claim 1, wherein said polypeptide is conjugated to a nucleic acid molecule, protein, peptide, small-molecule organic compound, fluorophore, metal-ligand complex, polysaccharide, nanoparticle, nanotube, polymer, cell, virus, virus-like particle or a combination thereof.

7. The polypeptide of claim 1, wherein the polypeptide is immobilised on a solid substrate.

8. A process for conjugating two molecules or components via an isopeptide bond comprising:
   a) providing a first molecule or component comprising a peptide tag comprising:
      (i) an amino acid sequence as set forth in SEQ ID NO: 2; or
      (ii) an amino acid sequence with at least 80% sequence identity to a sequence as set forth in SEQ ID NO: 2, wherein said amino acid sequence comprises a lysine residue at the position equivalent to position 9 of SEQ ID NO: 2;
   b) providing a second molecule or component comprising a peptide tag comprising:
      (i) an amino acid sequence as set forth in SEQ ID NO: 3; or
      (ii) an amino acid sequence with at least 80% sequence identity to a sequence as set forth in SEQ ID NO: 3, wherein said amino acid sequence comprises an asparagine residue at the position equivalent to position 17 of SEQ ID NO: 3;
   c) contacting said first and second molecules or components with a polypeptide as defined in claim 1, under conditions that enable the formation of an isopeptide bond between the lysine residue at the position equivalent to position 9 of SEQ ID NO: 2 and the asparagine residue at the position equivalent to position 17 of SEQ ID NO: 3, thereby conjugating said first molecule to said second molecule via an isopeptide to form a complex.

9. The process of claim 8, wherein the polypeptide is immobilised on a solid substrate, the process comprises a further step of separating the complex from the solid substrate, wherein said step comprises contacting said complex with a low pH buffer.

10. The process of claim 8, wherein the polypeptide is immobilised on a solid substrate, the process comprises a further step of separating the complex from the solid substrate, wherein said step comprises contacting said complex with a solution comprising imidazole.

11. The process of claim 8, wherein the polypeptide is immobilised on a solid substrate, the process comprises a further step of separating the complex from the solid substrate, wherein said step comprises contacting said complex with a solution comprising a competitor reaction product comprising a peptide having an amino acid sequence as set forth in SEQ ID NO: 2 ligated to a peptide having an amino acid sequence as set forth in SEQ ID NO: 3.

12. The process of claim 9 further comprising a step of washing the solid substrate with a buffer prior to separating said complex from the solid substrate.

13. The process of claim 8, wherein said first molecule comprises a peptide tag comprising an amino acid sequence as defined in a) conjugated to a nucleic acid molecule, protein, peptide, small-molecule organic compound, fluorophore, metal-ligand complex, polysaccharide, nanoparticle, nanotube, polymer, cell, virus, virus-like particle or a combination thereof.

14. The process of claim 8, wherein said second molecule comprises a peptide tag comprising an amino acid sequence as defined in b) conjugated to a nucleic acid molecule, protein, peptide, small-molecule organic compound, fluorophore, metal-ligand complex, polysaccharide, nanoparticle, nanotube, polymer, cell, virus, virus-like particle or a combination thereof.

15. A kit, wherein said kit comprises:
(a) a peptide ligase as defined in claim 1; and
(b) a peptide tag comprising:
(i) an amino acid sequence as set forth in SEQ ID NO: 2;
(ii) an amino acid sequence with at least 80% sequence identity to a sequence as set forth in SEQ ID NO: 2, wherein said amino acid sequence comprises a lysine residue at the position equivalent to position 9 of SEQ ID NO: 2,
(iii) an amino acid sequence as set forth in SEQ ID NO: 3; or
(iv) an amino acid sequence with at least 80% sequence identity to a sequence as set forth in SEQ ID NO: 3, wherein said amino acid sequence comprises an asparagine residue at the position equivalent to position 17 of SEQ ID NO: 3,
wherein said peptide tag is conjugated or fused to a molecule or component; and/or
(c) a nucleic acid molecule, encoding a peptide ligase as defined in (a); and
(d) a nucleic acid molecule, encoding a peptide tag as defined in (b).

16. The kit of claim 15 further comprising a second peptide tag conjugated or fused to a molecule or component, wherein the second peptide tag is capable of forming an isopeptide bond with the peptide tag in (b) when contacted with a peptide ligase of (a) under conditions suitable for the formation of an isopeptide bond.

17. The kit of claim 15, wherein the molecule or component is a nucleic acid molecule, protein, peptide, small-molecule organic compound, fluorophore, metal-ligand complex, polysaccharide, nanoparticle, nanotube, polymer, cell, virus, virus-like particle or a combination thereof.

18. The polypeptide of claim 1, wherein the polypeptide is in a lyophilized state.

* * * * *

SEQUENCE LISTING

```
<160> NUMBER OF SEQ ID NOS: 11

<210> SEQ ID NO 1
<211> LENGTH: 104
<212> TYPE: PRT
<213> ORGANISM: Artificial sequence
<220> FEATURE:
<223> OTHER INFORMATION: SnoopLigase

<400> SEQUENCE: 1

Val Asn Lys Asn Asp Lys Lys Pro Leu Arg Gly Ala Val Phe Ser Leu
1               5                   10                  15

Gln Lys Gln His Pro Asp Tyr Pro Asp Ile Tyr Gly Ala Ile Asp Gln
            20                  25                  30
```

Asn Gly Thr Tyr Gln Asn Val Arg Thr Gly Glu Asp Gly Lys Leu Thr
            35                  40                  45

Phe Lys Asn Leu Ser Asp Gly Lys Tyr Arg Leu Phe Glu Asn Ser Glu
 50                  55                  60

Pro Pro Gly Tyr Lys Pro Val Gln Asn Lys Pro Ile Val Ala Phe Gln
 65                  70                  75                  80

Ile Val Asn Gly Glu Val Arg Asp Val Thr Ser Ile Val Pro Pro Gly
                 85                  90                  95

Val Pro Ala Thr Tyr Glu Phe Thr
            100

<210> SEQ ID NO 2
<211> LENGTH: 12
<212> TYPE: PRT
<213> ORGANISM: Artificial sequence
<220> FEATURE:
<223> OTHER INFORMATION: SnoopTagJr

<400> SEQUENCE: 2

Lys Leu Gly Ser Ile Glu Phe Ile Lys Val Asn Lys
 1               5                  10

<210> SEQ ID NO 3
<211> LENGTH: 23
<212> TYPE: PRT
<213> ORGANISM: Artificial sequence
<220> FEATURE:
<223> OTHER INFORMATION: DogTag

<400> SEQUENCE: 3

Asp Ile Pro Ala Thr Tyr Glu Phe Thr Asp Gly Lys His Tyr Ile Thr
 1               5                  10                  15

Asn Glu Pro Ile Pro Pro Lys
            20

<210> SEQ ID NO 4
<211> LENGTH: 893
<212> TYPE: PRT
<213> ORGANISM: Streptococcus pneumoniae

<400> SEQUENCE: 4

Met Leu Asn Arg Glu Thr His Met Lys Lys Val Arg Lys Ile Phe Gln
 1               5                  10                  15

Lys Ala Val Ala Gly Leu Cys Cys Ile Ser Gln Leu Thr Ala Phe Ser
            20                  25                  30

Ser Ile Val Ala Leu Ala Glu Thr Pro Glu Thr Ser Pro Ala Ile Gly
            35                  40                  45

Lys Val Val Ile Lys Glu Thr Gly Glu Gly Gly Ala Leu Leu Gly Asp
 50                  55                  60

Ala Val Phe Glu Leu Lys Asn Asn Thr Asp Gly Thr Thr Val Ser Gln
 65                  70                  75                  80

Arg Thr Glu Ala Gln Thr Gly Glu Ala Ile Phe Ser Asn Ile Lys Pro
                 85                  90                  95

Gly Thr Tyr Thr Leu Thr Glu Ala Gln Pro Pro Val Gly Tyr Lys Pro
            100                 105                 110

Ser Thr Lys Gln Trp Thr Val Glu Val Glu Lys Asn Gly Arg Thr Thr
        115                 120                 125

Val Gln Gly Glu Gln Val Glu Asn Arg Glu Glu Ala Leu Ser Asp Gln
    130                 135                 140

-continued

```
Tyr Pro Gln Thr Gly Thr Tyr Pro Asp Val Gln Thr Pro Tyr Gln Ile
145                 150                 155                 160

Ile Lys Val Asp Gly Ser Glu Lys Asn Gly Gln His Lys Ala Leu Asn
                165                 170                 175

Pro Asn Pro Tyr Glu Arg Val Ile Pro Glu Gly Thr Leu Ser Lys Arg
            180                 185                 190

Ile Tyr Gln Val Asn Asn Leu Asp Asp Asn Gln Tyr Gly Ile Glu Leu
        195                 200                 205

Thr Val Ser Gly Lys Thr Val Tyr Glu Gln Lys Asp Lys Ser Val Pro
210                 215                 220

Leu Asp Val Val Ile Leu Leu Asp Asn Ser Asn Ser Met Ser Asn Ile
225                 230                 235                 240

Arg Asn Lys Asn Ala Arg Arg Ala Glu Arg Ala Gly Glu Ala Thr Arg
                245                 250                 255

Ser Leu Ile Asp Lys Ile Thr Ser Asp Ser Glu Asn Arg Val Ala Leu
            260                 265                 270

Val Thr Tyr Ala Ser Thr Ile Phe Asp Gly Thr Glu Phe Thr Val Glu
        275                 280                 285

Lys Gly Val Ala Asp Lys Asn Gly Lys Arg Leu Asn Asp Ser Leu Phe
290                 295                 300

Trp Asn Tyr Asp Gln Thr Ser Phe Thr Thr Asn Thr Lys Asp Tyr Ser
305                 310                 315                 320

Tyr Leu Lys Leu Thr Asn Asp Lys Asn Asp Ile Val Glu Leu Lys Asn
                325                 330                 335

Lys Val Pro Thr Glu Ala Glu Asp His Asp Gly Asn Arg Leu Met Tyr
            340                 345                 350

Gln Phe Gly Ala Thr Phe Thr Gln Lys Ala Leu Met Lys Ala Asp Glu
        355                 360                 365

Ile Leu Thr Gln Gln Ala Arg Gln Asn Ser Gln Lys Val Ile Phe His
370                 375                 380

Ile Thr Asp Gly Val Pro Thr Met Ser Tyr Pro Ile Asn Phe Asn His
385                 390                 395                 400

Ala Thr Phe Ala Pro Ser Tyr Gln Asn Gln Leu Asn Ala Phe Phe Ser
                405                 410                 415

Lys Ser Pro Asn Lys Asp Gly Ile Leu Leu Ser Asp Phe Ile Thr Gln
            420                 425                 430

Ala Thr Ser Gly Glu His Thr Ile Val Arg Gly Asp Gly Gln Ser Tyr
        435                 440                 445

Gln Met Phe Thr Asp Lys Thr Val Tyr Glu Lys Gly Ala Pro Ala Ala
450                 455                 460

Phe Pro Val Lys Pro Glu Lys Tyr Ser Glu Met Lys Ala Ala Gly Tyr
465                 470                 475                 480

Ala Val Ile Gly Asp Pro Ile Asn Gly Gly Tyr Ile Trp Leu Asn Trp
                485                 490                 495

Arg Glu Ser Ile Leu Ala Tyr Pro Phe Asn Ser Asn Thr Ala Lys Ile
            500                 505                 510

Thr Asn His Gly Asp Pro Thr Arg Trp Tyr Tyr Asn Gly Asn Ile Ala
        515                 520                 525

Pro Asp Gly Tyr Asp Val Phe Thr Val Gly Ile Gly Ile Asn Gly Asp
530                 535                 540

Pro Gly Thr Asp Glu Ala Thr Ala Thr Ser Phe Met Gln Ser Ile Ser
545                 550                 555                 560

Ser Lys Pro Glu Asn Tyr Thr Asn Val Thr Asp Thr Thr Lys Ile Leu
```

```
                    565                 570                 575
Glu Gln Leu Asn Arg Tyr Phe His Thr Ile Val Thr Glu Lys Lys Ser
                580                 585                 590

Ile Glu Asn Gly Thr Ile Thr Asp Pro Met Gly Glu Leu Ile Asp Leu
                595                 600                 605

Gln Leu Gly Thr Asp Gly Arg Phe Asp Pro Ala Asp Tyr Thr Leu Thr
            610                 615                 620

Ala Asn Asp Gly Ser Arg Leu Glu Asn Gly Gln Ala Val Gly Gly Pro
625                 630                 635                 640

Gln Asn Asp Gly Gly Leu Leu Lys Asn Ala Lys Val Leu Tyr Asp Thr
                645                 650                 655

Thr Glu Lys Arg Ile Arg Val Thr Gly Leu Tyr Leu Gly Thr Asp Glu
                660                 665                 670

Lys Val Thr Leu Thr Tyr Asn Val Arg Leu Asn Asp Glu Phe Val Ser
                675                 680                 685

Asn Lys Phe Tyr Asp Thr Asn Gly Arg Thr Thr Leu His Pro Lys Glu
                690                 695                 700

Val Glu Gln Asn Thr Val Arg Asp Phe Pro Ile Pro Lys Ile Arg Asp
705                 710                 715                 720

Val Arg Lys Tyr Pro Glu Ile Thr Ile Ser Lys Glu Lys Lys Leu Gly
                725                 730                 735

Asp Ile Glu Phe Ile Lys Val Asn Lys Asn Asp Lys Lys Pro Leu Arg
            740                 745                 750

Gly Ala Val Phe Ser Leu Gln Lys Gln His Pro Asp Tyr Pro Asp Ile
            755                 760                 765

Tyr Gly Ala Ile Asp Gln Asn Gly Thr Tyr Gln Asn Val Arg Thr Gly
        770                 775                 780

Glu Asp Gly Lys Leu Thr Phe Lys Asn Leu Ser Asp Gly Lys Tyr Arg
785                 790                 795                 800

Leu Phe Glu Asn Ser Glu Pro Ala Gly Tyr Lys Pro Val Gln Asn Lys
                805                 810                 815

Pro Ile Val Ala Phe Gln Ile Val Asn Gly Glu Val Arg Asp Val Thr
            820                 825                 830

Ser Ile Val Pro Gln Asp Ile Pro Ala Gly Tyr Glu Phe Thr Asn Asp
            835                 840                 845

Lys His Tyr Ile Thr Asn Glu Pro Ile Pro Lys Arg Glu Tyr Pro
            850                 855                 860

Arg Thr Gly Gly Ile Gly Met Leu Pro Phe Tyr Leu Ile Gly Cys Met
865                 870                 875                 880

Met Met Gly Gly Val Leu Leu Tyr Thr Arg Lys His Pro
                885                 890

<210> SEQ ID NO 5
<211> LENGTH: 312
<212> TYPE: DNA
<213> ORGANISM: Artificial sequence
<220> FEATURE:
<223> OTHER INFORMATION: SnoopLigase

<400> SEQUENCE: 5
gtgaataaga acgataaaaa gccgctgcgt ggtgccgtgt ttagcctgca gaaacagcat      60
cccgactatc ccgatatcta tggcgcgatt gatcagaatg gaacctatca aaatgtgcgt     120
accggcgaag atggtaaact gacctttaag aatctgagcg atggcaaata tcgcctgttt     180
gaaaatagcg aaccccccggg ctataaaccg gtgcagaata agccgattgt ggcgtttcag     240
```

```
attgtgaatg gcgaagtgcg tgatgtgacc agcattgtgc cgccgggtgt gccggctaca    300
tatgaattta cc                                                       312
```

<210> SEQ ID NO 6
<211> LENGTH: 36
<212> TYPE: DNA
<213> ORGANISM: Artificial sequence
<220> FEATURE:
<223> OTHER INFORMATION: SnoopTagJr

<400> SEQUENCE: 6

```
aaactgggct ctattgaatt tattaaagtg aacaaa                              36
```

<210> SEQ ID NO 7
<211> LENGTH: 69
<212> TYPE: DNA
<213> ORGANISM: Artificial sequence
<220> FEATURE:
<223> OTHER INFORMATION: DogTag

<400> SEQUENCE: 7

```
gatattccgg ctacatatga atttaccgat ggtaaacatt atatcaccaa tgaaccgata    60
ccgccgaaa                                                            69
```

<210> SEQ ID NO 8
<211> LENGTH: 104
<212> TYPE: PRT
<213> ORGANISM: Artificial sequence
<220> FEATURE:
<223> OTHER INFORMATION: RrgALigase

<400> SEQUENCE: 8

Val Asn Lys Asn Asp Lys Lys Pro Leu Arg Gly Ala Val Phe Ser Leu
1               5                   10                  15

Gln Lys Gln His Pro Asp Tyr Pro Asp Ile Tyr Gly Ala Ile Asp Gln
            20                  25                  30

Asn Gly Thr Tyr Gln Asn Val Arg Thr Gly Glu Asp Gly Lys Leu Thr
        35                  40                  45

Phe Lys Asn Leu Ser Asp Gly Lys Tyr Arg Leu Phe Glu Asn Ser Glu
    50                  55                  60

Pro Ala Gly Tyr Lys Pro Val Gln Asn Lys Pro Ile Val Ala Phe Gln
65                  70                  75                  80

Ile Val Asn Gly Glu Val Arg Asp Val Thr Ser Ile Val Pro Gln Asp
                85                  90                  95

Ile Pro Ala Thr Tyr Glu Phe Thr
            100

<210> SEQ ID NO 9
<211> LENGTH: 12
<212> TYPE: PRT
<213> ORGANISM: Artificial sequence
<220> FEATURE:
<223> OTHER INFORMATION: SnoopTag

<400> SEQUENCE: 9

Lys Leu Gly Asp Ile Glu Phe Ile Lys Val Asn Lys
1               5                   10

<210> SEQ ID NO 10
<211> LENGTH: 23
<212> TYPE: PRT

```
<213> ORGANISM: Artificial sequence
<220> FEATURE:
<223> OTHER INFORMATION: RrgATag2

<400> SEQUENCE: 10

Asp Ile Pro Ala Thr Tyr Glu Phe Thr Asn Gly Lys His Tyr Ile Thr
1               5                   10                  15

Asn Glu Pro Ile Pro Pro Lys
            20

<210> SEQ ID NO 11
<211> LENGTH: 15
<212> TYPE: PRT
<213> ORGANISM: Artificial sequence
<220> FEATURE:
<223> OTHER INFORMATION: SnoopTag solid-phase synthesised peptide

<400> SEQUENCE: 11

Gly Lys Leu Gly Asp Ile Glu Phe Ile Lys Val Asn Lys Gly Tyr
1               5                   10                  15
```